(12) United States Patent
Nygaard

(10) Patent No.: US 9,372,160 B2
(45) Date of Patent: Jun. 21, 2016

(54) METHOD AND SYSTEM FOR OPTICALLY INSPECTING THE ENDS OF A MANUFACTURED PART AT A SINGLE INSPECTION STATION HAVING A MEASUREMENT AXIS

(71) Applicant: GII ACQUISITION, LLC, Davisburg, MI (US)

(72) Inventor: Michael G. Nygaard, Grand Blanc, MI (US)

(73) Assignee: GII ACQUISITION, LLC, Davisburg, MI (US)

( * ) Notice: Subject to any disclaimer, the term of this patent is extended or adjusted under 35 U.S.C. 154(b) by 0 days.

(21) Appl. No.: 14/876,192

(22) Filed: Oct. 6, 2015

(65) Prior Publication Data

US 2016/0109383 A1   Apr. 21, 2016

Related U.S. Application Data

(63) Continuation-in-part of application No. 14/629,527, filed on Feb. 24, 2015, which is a continuation-in-part of application No. 14/050,907, filed on Oct. 10, 2013, now Pat. No. 9,019,489, which is a continuation of (Continued)

(51) Int. Cl.
*G01B 11/24* (2006.01)
*G01N 21/952* (2006.01)

(52) U.S. Cl.
CPC ...... *G01N 21/952* (2013.01); *G01N 2201/0621* (2013.01)

(58) Field of Classification Search
CPC ...... G01B 11/24; G01B 11/25; G01B 11/306; G01B 11/245; G06T 7/0057

USPC .................................................... 356/601
See application file for complete search history.

(56) References Cited

U.S. PATENT DOCUMENTS

| 2,449,255 A | 9/1948 | Sneckner |
| 3,411,009 A | 11/1968 | Ford et al. |

(Continued)

FOREIGN PATENT DOCUMENTS

| EP | 0047936 A1 | 3/1982 |
| JP | 2008073653 A | 4/2008 |

(Continued)

OTHER PUBLICATIONS

Extended European Search Report; related EP application No. 13757558.5; date of completion of search Sep. 1, 2015.

(Continued)

*Primary Examiner* — Tarifur Chowdhury
*Assistant Examiner* — MD M Rahman
(74) *Attorney, Agent, or Firm* — Brooks Kushman P.C.

(57) ABSTRACT

A method and system for optically inspecting the ends of a manufactured part at a single inspection station having a measurement axis are provided. The system includes a fixture assembly having a rotatable first fixturing component and a rotatable second fixturing component mating with and removably connected to the first fixturing component to transmit torque from the first fixturing component to the second fixturing component. The second fixturing component has a device for holding the part in a generally horizontal orientation and permit rotation of the horizontally held part between first and second angular positions about the measurement axis. The system also includes an actuator assembly, an illumination device, a lens and detector assembly and at least one processor to process electrical signals generated by the lens and detector assembly to determine at least one geometric dimension or any visual defects at the ends of the part.

20 Claims, 15 Drawing Sheets

Related U.S. Application Data application No. 13/109,369, filed on May 17, 2011, now Pat. No. 8,570,504, said application No. 14/876,192 is a continuation-in-part of application No. 13/414,081, filed on Mar. 7, 2012.

(56) References Cited

U.S. PATENT DOCUMENTS

| | | | |
|---|---|---|---|
| 3,604,940 A | 9/1971 | Matthews | |
| 3,924,953 A | 12/1975 | Allard | |
| 4,280,624 A | 7/1981 | Ford | |
| 4,315,688 A | 2/1982 | Pryor | |
| 4,480,912 A * | 11/1984 | Snyder, Jr. | G01B 11/26 356/138 |
| 4,547,674 A | 10/1985 | Pryor et al. | |
| 4,598,998 A | 7/1986 | Kamei et al. | |
| 4,636,635 A | 1/1987 | Kronseder | |
| 4,644,394 A | 2/1987 | Reeves | |
| 4,666,363 A * | 5/1987 | Johansson | B23K 37/0452 198/378 |
| 4,691,231 A | 9/1987 | Fitzmorris et al. | |
| 4,721,388 A | 1/1988 | Takagi et al. | |
| 4,769,743 A * | 9/1988 | Callahan | F21S 2/005 362/18 |
| 4,827,387 A * | 5/1989 | Ferren | F21V 21/30 362/277 |
| 4,831,251 A | 5/1989 | Hanna | |
| 4,849,864 A * | 7/1989 | Forrest | F21S 8/00 363/225 |
| 4,852,983 A | 8/1989 | Fein | |
| 4,906,098 A | 3/1990 | Thomas et al. | |
| 4,912,318 A | 3/1990 | Kajiura et al. | |
| 4,923,066 A | 5/1990 | Ophir et al. | |
| 4,969,746 A | 11/1990 | McConnell et al. | |
| 4,970,401 A | 11/1990 | Sadeh et al. | |
| 4,983,043 A | 1/1991 | Harding | |
| 5,012,117 A | 4/1991 | Karafa et al. | |
| 5,024,529 A | 6/1991 | Svetkoff et al. | |
| 5,098,031 A | 3/1992 | Hitomi | |
| 5,164,995 A | 11/1992 | Brooks et al. | |
| 5,168,458 A | 12/1992 | Gomes | |
| 5,170,306 A | 12/1992 | Gomes | |
| 5,291,272 A | 3/1994 | Demirsu | |
| 5,383,021 A | 1/1995 | Hanna | |
| 5,521,707 A | 5/1996 | Castore et al. | |
| 5,546,189 A | 8/1996 | Svetkoff et al. | |
| 5,568,263 A | 10/1996 | Hanna | |
| 5,608,530 A | 3/1997 | Gates | |
| 5,617,209 A | 4/1997 | Svetkoff et al. | |
| 5,646,724 A | 7/1997 | Hershline | |
| 5,802,698 A * | 9/1998 | Fitzgerald | B23Q 1/58 269/71 |
| 5,815,275 A | 9/1998 | Svetkoff et al. | |
| 5,975,710 A | 11/1999 | Luster | |
| 5,986,753 A * | 11/1999 | Seelig | G01B 5/0002 356/244 |
| 6,038,521 A | 3/2000 | Kanai | |
| 6,055,329 A | 4/2000 | Mufti | |
| 6,098,031 A | 8/2000 | Svetkoff et al. | |
| 6,122,045 A | 9/2000 | Pike et al. | |
| 6,285,034 B1 | 9/2001 | Hanna et al. | |
| 6,289,600 B1 | 9/2001 | Watts | |
| 6,313,948 B1 | 11/2001 | Hanna | |
| 6,959,108 B1 | 10/2005 | Bartelt et al. | |
| 7,065,242 B2 | 6/2006 | Petrov et al. | |
| 7,140,119 B2 * | 11/2006 | Badami | G01B 21/045 33/503 |
| 7,173,692 B2 | 2/2007 | Yasuda et al. | |
| 7,312,607 B2 | 12/2007 | Nygaard | |
| 7,329,855 B2 | 2/2008 | Katayama et al. | |
| 7,403,872 B1 | 7/2008 | St. Onge et al. | |
| 7,633,046 B2 | 12/2009 | Spalding | |
| 7,633,634 B2 | 12/2009 | Spalding et al. | |
| 7,633,635 B2 | 12/2009 | Nygaard et al. | |
| 7,684,054 B2 | 3/2010 | Crowther | |
| 7,738,088 B2 | 6/2010 | Spalding | |
| 7,738,121 B2 | 6/2010 | Spalding | |
| 7,755,754 B2 | 7/2010 | Spalding | |
| 7,777,900 B2 | 8/2010 | Nygaard et al. | |
| 7,796,278 B2 | 9/2010 | Spalding et al. | |
| 8,004,694 B2 | 8/2011 | Lee et al. | |
| 8,054,460 B2 | 11/2011 | Agapiou et al. | |
| 8,132,802 B2 | 3/2012 | Kolodge et al. | |
| 8,179,434 B2 | 5/2012 | Koval et al. | |
| 8,550,444 B2 | 10/2013 | Nygaard et al. | |
| 8,570,504 B2 | 10/2013 | Nygaard | |
| 8,723,068 B2 | 5/2014 | Nygaard | |
| 8,896,844 B2 | 11/2014 | Nygaard et al. | |
| 9,019,489 B2 | 4/2015 | Nygaard | |
| 2003/0039388 A1 | 2/2003 | Ulrich et al. | |
| 2004/0022427 A1 | 2/2004 | Yang et al. | |
| 2004/0066505 A1 | 4/2004 | Berg et al. | |
| 2004/0223143 A1 | 11/2004 | Yasuda et al. | |
| 2005/0174567 A1 | 8/2005 | Hanna | |
| 2006/0236792 A1 | 10/2006 | Hanna | |
| 2008/0013820 A1 | 1/2008 | Vertoprakhov et al. | |
| 2009/0103107 A1 | 4/2009 | Nygaard | |
| 2009/0103112 A1 | 4/2009 | Nygaard | |
| 2010/0201806 A1 | 8/2010 | Nygaard et al. | |
| 2010/0238435 A1 | 9/2010 | Spalding | |
| 2010/0245850 A1 | 9/2010 | Lee et al. | |
| 2012/0105429 A1 | 5/2012 | Nygaard | |
| 2012/0293623 A1 | 11/2012 | Nygaard | |
| 2012/0293789 A1 | 11/2012 | Nygaard | |
| 2013/0235371 A1 | 9/2013 | Nygaard et al. | |
| 2014/0063509 A1 | 3/2014 | Nygaard et al. | |

FOREIGN PATENT DOCUMENTS

| | | |
|---|---|---|
| WO | WO2005022076 A2 | 3/2005 |
| WO | WO2009130062 A1 | 10/2009 |

OTHER PUBLICATIONS

Wilson, Andrew; "Lens Designs Tackle Novel Vision Applications"; Vision Systems Design; Jul. 1, 2011; URL: http://www.vision-systems.com/articles/print/volume-16/issue-7/features/lens-designs-tackle-novel-vision-applications.html.

Notice of Allowance and Fee(s) Due; related U.S. Appl. No. 14/876,187; date mailed: Mar. 15, 2016.

* cited by examiner

METHOD AND SYSTEM FOR OPTICALLY INSPECTING THE ENDS OF A MANUFACTURED PART AT A SINGLE INSPECTION STATION HAVING A MEASUREMENT AXIS

CROSS-REFERENCE TO RELATED APPLICATION

This application is a continuation-in-part of U.S. patent application Ser. No. 14/629,527 filed Feb. 24, 2015. This application is related to U.S. patent application Ser. No.14/876,187 filed Oct. 6, 2015.

TECHNICAL FIELD

This invention generally relates to non-contact methods and systems for optically inspecting the ends of manufactured parts such as ammunition cases and threaded fasteners at a single inspection station.

Overview

Traditional manual, gauging devices and techniques have been replaced to some extent by automatic inspection methods and systems. However, such automatic inspection methods and systems still have a number of shortcomings associated with them.

Many parts, such as fasteners and ammunition cartridges and cases develop cracks, splits, or other outer surface defects during the manufacturing process. While parts can be linearly moved along their axes during the inspection process, this adds additional time to the process.

In optical metrology, inter-reflection (i.e., double bounce or secondary reflection) poses a challenge for surface measurement of shiny objects. Due to specular reflections that can occur among concave surfaces or combinations of surfaces positioned near right angles to each other, the true desired laser lines are often obscured by inter-reflection lines. Such obscuration makes it difficult to measure shiny surfaces of complex surface geometry.

Laser triangulation measuring equipment generally operate by projecting, with a laser beam having a wavelength centered at approximately 830 nm (infrared (IR) radiation), a light spot having a preset spot size onto the surface to be examined, e.g., from a laser projection "gun" that may be mounted normal to the surface being examined. A light detection unit including a lens and a light detecting element or "camera," such as a CCD or CMOS imaging chip or a position sensing device (PSD), e.g., of silicon, at an offset angle to the projection axis may observe the position of the laser spot in its field of view and output a signal describing the angle at which the spot appeared in the field of view. The range to the object can be computed from the angle information when the distance between the laser projection axis and the light detection unit is known. The offset angle between the laser beam and the line of sight of the light detection unit is often referred to as the "triangulation angle." Based on which part of the detector the light reflected from the imaged object impinges, the height or "z-component" of the object at the point at which the light spot impinges upon the object may be determined.

Inspection of defects on and in small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the U.S. Department of Defense, MIL-STD-636. For small arms ammunition calibers up to 0.50, this standard serves to evaluate and illustrate a practical majority of defects assembled as a result of extensive surveys covering all the small arms ammunition manufacturing facilities in the United States.

As explained in the above-noted military standard, a case is counted as a defective because of a split case if the cartridge case shows a definite separation of the metal entirely through the case wall. A case is classified as either a "major" or "critical" defect depending on the location of split.

U.S. Pat. No. 4,923,066 discloses an automatic visual inspection system for small arms ammunition which sorts visual surface flaws at high speed according to established standards which can be tailored to fit specific needs.

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Pat. No. 4,852,983 discloses an optical system which simulates the optical effect of traveling over a large distance on light traveling between reference surfaces.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

U.S. Pat. No. 6,289,600 discloses a non-contact measuring device for determining the dimensions of a cylindrical object, such as a pipe.

U.S. Pat. No. 5,521,707 discloses a non-contact laser-based sensor guided by a precision mechanical system to scan a thread form producing a set of digitized images of the thread form.

WO 2009/130062 discloses a method and a device for the optical viewing of objects.

As described in U.S. Pat. No. 6,098,031, triangulation is the most commonly used 3-D imaging method and offers a good figure of merit for resolution and speed. U.S. Pat. Nos. 5,024,529 and 5,546,189 describe the use of triangulation-based systems for inspection of many industrial parts, including shiny surfaces like pins of a grid array. U.S. Pat. No. 5,617,209 shows a scanning method for grid arrays which has additional benefits for improving accuracy. The method of using an angled beam of radiant energy can be used for triangulation, confocal or general line scan systems. Unfortunately, triangulation systems are not immune to fundamental limitations like occlusion and sensitivity to background reflection. Furthermore, at high magnification, the depth of focus can limit performance of systems, particularly edge location accuracy, when the object has substantial relief and a wide dynamic range (i.e. variation in surface reflectance). In some cases, camera-based systems have been combined with triangulation systems to enhance measurement capability.

U.S. Pat. No. 5,098,031 discloses a method and system for high-speed, 3-D imaging of microscopic targets. The system includes confocal and triangulation-based scanners or subsystems which provide data which is both acquired and processed under the control of a control algorithm to obtain information such as dimensional information about the microscopic targets which may be "non-cooperative." The "non-cooperative" targets are illuminated with a scanning beam of electromagnetic radiation such as laser light incident from a first direction. A confocal detector of the electromagnetic radiation is placed at a first location for receiving reflected radiation which is substantially optically collinear with the incident beam of electromagnetic radiation. The triangulation-based subsystem also includes a detector of electromagnetic radiation which is placed at a second location which is non-collinear with respect to the incident beam. Digital data is derived from signals produced by the detectors.

U.S. Pat. No. 5,815,275 discloses triangulation-based 3-D imaging using an angled scanning beam of radiant energy.

Published U.S. Patent Applications 2009/0103107 and 2009/0103112 disclose part inspection using a profile inspection subsystem and triangulation.

U.S. Pat. No. 4,547,674 discloses a method and apparatus for inspecting gear geometry via optical triangulation.

U.S. Pat. No. 4,970,401 discloses a non-contact triangulation probe system including a base plate and a first non-contact triangulation probe including a light source mounted on a first movable slide.

U.S. Pat. Nos. 5,168,458 and 5,170,306 disclose methods and systems for gauging threaded fasteners to obtain trilobular parameters.

Other U.S. patent documents related to the invention include: U.S. Pat. Nos. 2,449,255; 3,411,009; 3,604,940; 4,280,624; 4,315,688; 4,598,998; 4,636,635; 4,644,394; 4,691,231; 4,852,983; 4,906,098; 4,912,318; 4,923,066; 4,969,746; 5,521,707; 5,608,530; 5,646,724; 5,291,272; 6,055,329; 4,983,043; 3,924,953; 5,164,995; 4,721,388; 4,969,746; 5,012,117; 5,975,710; 6,038,521; 6,122,045; 7,173,692; 7,329,855; 7,738,121; 6,055,329; 7,065,242; 8,723,068; 7,684,054; 7,403,872; 7,633,635; 7,312,607; 7,777,900; 7,633,046; 7,633,634; 7,738,121; 7,755,754; 7,738,088; 7,796,278; 7,684,054; 8,054,460; 8,132,802; 8,179,434; 8,550,444; 8,570,504; 8,896,844; 9,019,489; and U.S. published patent applications 2004/0066505; 2008/0013820; 2010/0245850, 2010/0201806, 2012/0293623; 2012/0105429; 2012/0293789; 2013/0235371; and 2014/0063509.

SUMMARY OF EXAMPLE EMBODIMENTS

An object of at least one embodiment of the present invention is to provide a method and system for optically inspecting the ends of a manufactured part at a single inspection station at which the part is easily fixtured to have a generally horizontal orientation to obtain end views of the part.

In carrying out the above object and other objects of at least one embodiment of the present invention, a method of optically inspecting the ends of a manufactured part at a single inspection station having a measurement axis is provided. The part has opposite top and bottom ends with top and bottom end surfaces, respectively, a length between the ends, a width and a part axis. The method includes the step of holding the part in a generally horizontal orientation. The method also includes rotating the horizontally held part about the measurement axis so that the part moves between first and second angular positions and directing a beam of radiation at the top end surface of the horizontally held part at the first angular position and at the bottom end surface of the horizontally held part at the second angular position to obtain first and second reflected beams, respectively. The method further includes detecting the first and second reflected beams at the inspection station to obtain electrical signals and processing the electrical signals to determine at least one geometric dimension or any visual defects at the ends of the part.

The first and second reflected beams may be detected at a single image plane. The image plane may have a predetermined position and orientation at the measurement station during each of the steps.

The part axis may be defined as being central to the part and parallel to its length.

The method may further include projecting focused lines of radiation at the top and bottom end surfaces of the held part to obtain reflected radiation and sensing the reflected radiation to obtain electrical signals which represent a depth feature of the part.

The beams of radiation at the top and bottom end surfaces may be strobed.

Further in carrying out the above object and other objects of at least one embodiment of the present invention, a system for optically inspecting the ends of a manufactured part at a single inspection station having a measurement axis is provided. The part has opposite top and bottom ends with top and bottom end surfaces, respectively, a length between the ends, a width and a part axis. The system includes a fixture assembly having a rotatable first fixturing component. The assembly also includes a rotatable second fixturing component mating with and removably connected to the first fixturing component to transmit torque from the first fixturing component to the second fixturing component. The second fixturing component includes a device for holding the part in a generally horizontal orientation and permit rotation of the horizontally held part between first and second angular positions about the measurement axis. The system further includes an actuator assembly to rotatably drive the first fixturing component about the measurement axis and to rotatably drive the second fixturing component about the measurement axis between the first and second angular positions when the second fixturing component is connected to the first fixturing component. The system still further includes an illumination device to direct a beam of radiation at the top end surface of the horizontally held part at the first angular position and at the bottom end surface of the horizontally held part at the second angular position to obtain first and second reflected beams, respectively. The system further includes a lens and detector assembly to image and detect the reflected beams to obtain electrical signals and at least one processor to process the electrical signals to determine at least one geometric dimension or any visual defects at the ends of the part.

The lens and detector assembly may have a predetermined position, orientation and field of view at the inspection station wherein the second fixturing component holds the part inside the predetermined field of view in the first and second angular positions.

The first and second reflected beams may be detected at a single image plane of the lens and detector assembly.

The part axis may be defined as being central to the part and parallel to its length.

The system may further include an optical depth sensor to sense a depth feature of the part.

The depth sensor may include a triangulation-based sensor configured to project focused lines of radiation at the top and bottom end surfaces of the held part and to sense corresponding reflected lines of radiation to obtain electrical signals.

The beams of radiation may be strobed.

The illumination device may include an array of spaced light sources.

Each of the light sources may be a light emitting diode.

The light sources may be arranged in a generally curved arrangement.

The actuator assembly may include an electrically-powered, rotary actuator.

The first fixturing component may comprise a mating tool.

The tool may comprise a recess bit.

The device may comprise a V-block.

BRIEF DESCRIPTION OF THE DRAWINGS

For a more complete understanding of the present invention, and for further features and advantages thereof, reference is made to the following description taken in conjunction with the accompanying drawings, in which.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 19:
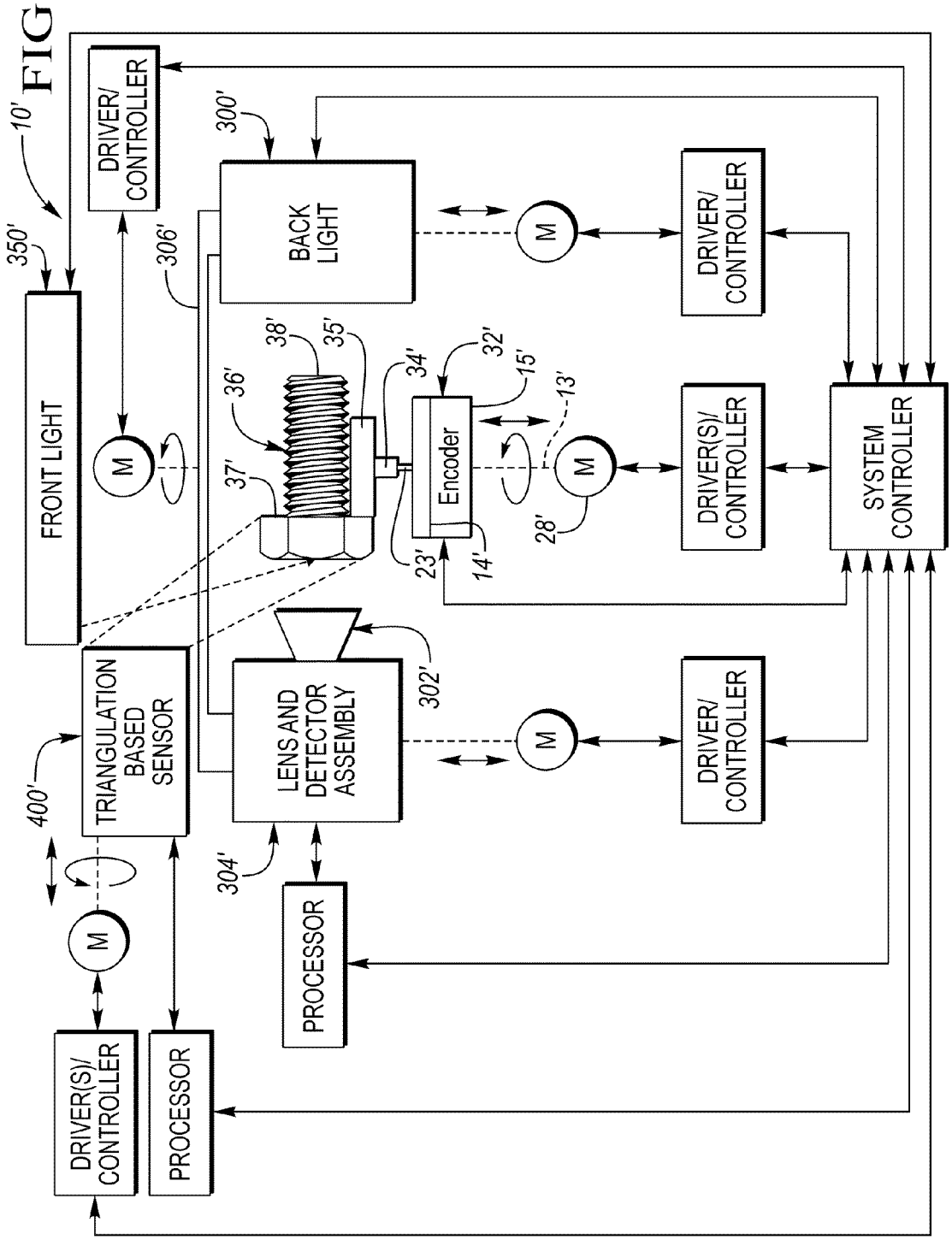
FIG. 19 is a side schematic, block diagram view of another embodiment of the method and system of the present invention with the same optical inspection devices of FIGS. 3, 8, and 17 and additional electronics and actuator assemblies but with a different lower tooling assembly or fixture including a V-block supported on a shaft with a hex on one end thereof to receive and retain the recess bit in mating engagement to allow the optical inspection of the ends of the held part.

In general, and as described below, at least one embodiment of the present invention provides a non-contact method and system for optically inspecting the ends of a manufactured part at a single inspection station having a measurement axis 13 (FIG. 17) or 13' (FIG. 19). A common set of optical inspection devices of the first and second embodiments of the system is illustrated in FIGS. 3, 8, 17 and 19 but not within the enclosure of FIG. 2 for purposes of simplicity. The optical inspection devices include a high speed, high resolution camera 304, a lens 302, an optical depth sensor 400 (such as a triangulation-based sensor), back lighting 300 and front lighting 350. A first embodiment of the system is generally indicated at 10 in FIG. 17 and a second embodiment of the system is generally indicated at 10' in FIG. 19.

In general, parts of the two embodiments which are substantially the same in either structure or function have the same reference number but the parts of the second embodiment have a single prime designation. An example part, such as a threaded fastener or bolt 36, has threads 38, a length between its ends, a width, and a part axis which, preferably, is central to the part and parallel to its length. A bolt or part 36' also has top and bottom ends with top and bottom surfaces 39' and 41', respectively (i.e. FIGS. 8-11). While a variety of manufactured parts which may be inspected are shown in the drawing figures, including FIG. 1, all of the parts are given either reference number 36 or 36'.

The threaded bolt 36 is initially held or supported by upper and lower components or tooling 31 and 23, respectively, of a chuck or fixture assembly, generally included at 32. The lower component part or recess bit 23 is typically mounted on a stage 14 to rotate therewith to provide side profile views of the held part. An encoder 15 provides an output signal based on the amount of rotary movement.

Figure 9:
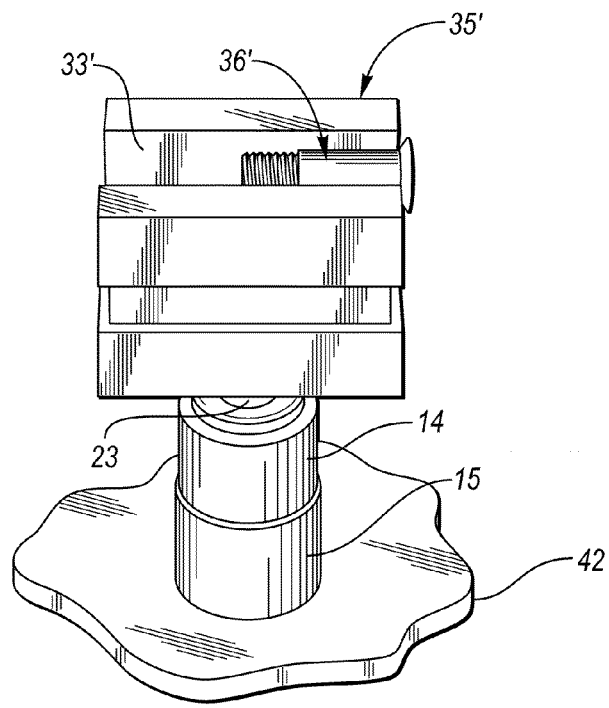
FIG. 9 is an enlarged view, partially broken away, of a portion of the view of FIG. 8 to further illustrate the V-block, the part held thereby, the recess bit, the rotary stage and the rotary encoder.
Figure 10:
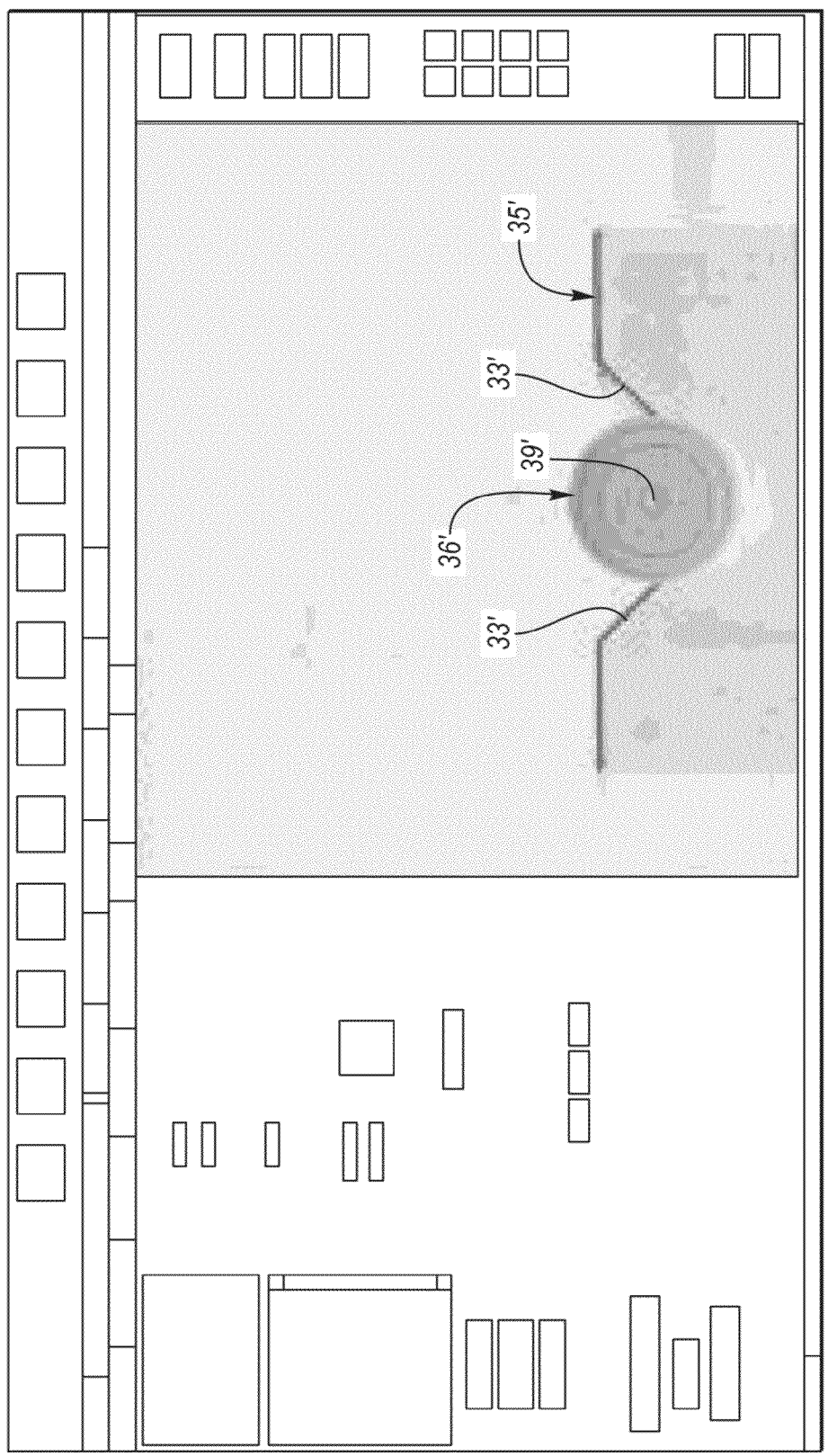
FIG. 10 is a schematic view of a screen shot (without displayed icons or data) which shows one end (top) view of an inspected part as it is being held horizontally by the V-block between angled surfaces.
Figure 11:
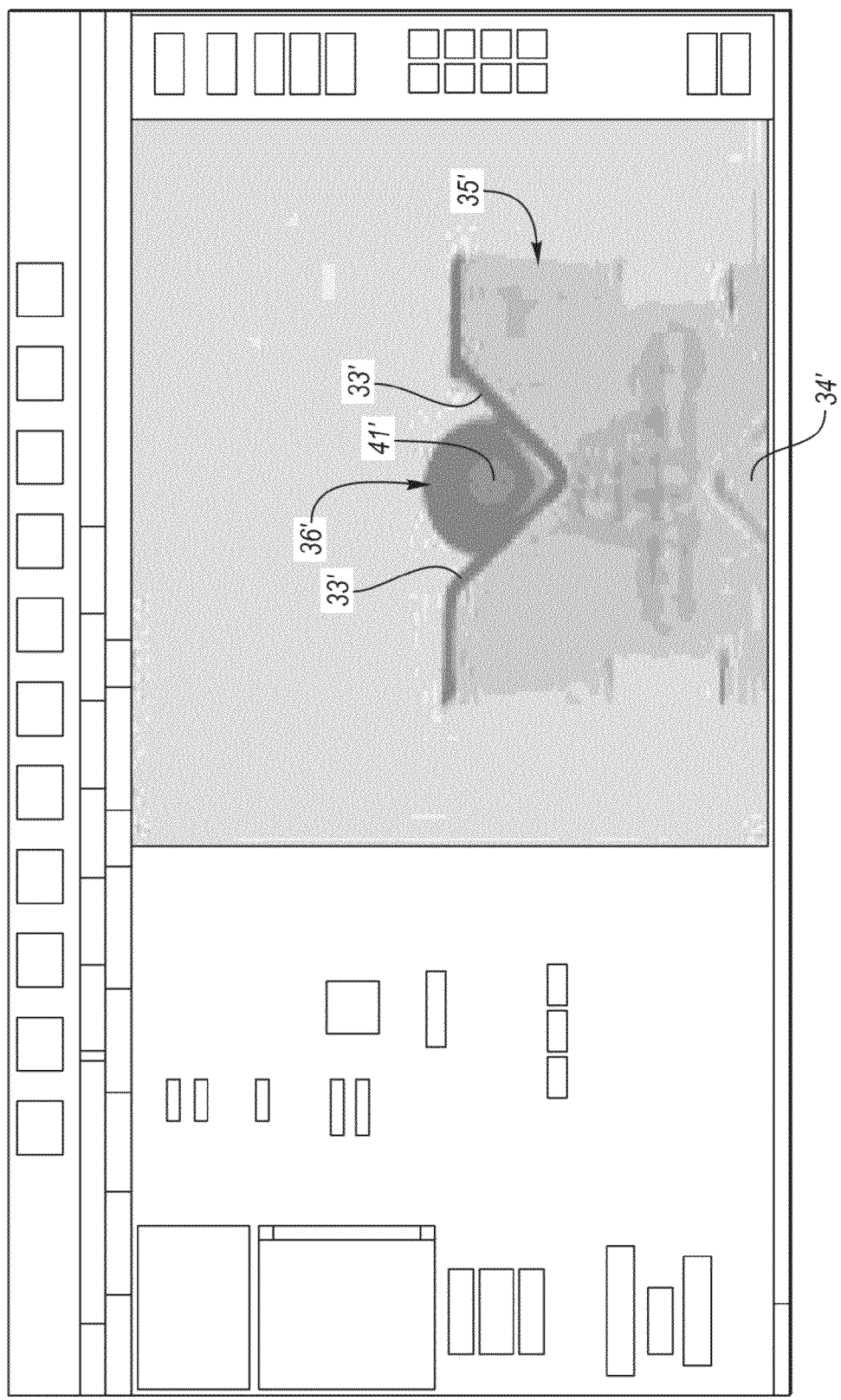
FIG. 11 is a schematic view of a screen shot (without displayed icons or data) which shows an opposite end (bottom) view of the inspected part as its being held horizontally by the V-block.
Figure 12:
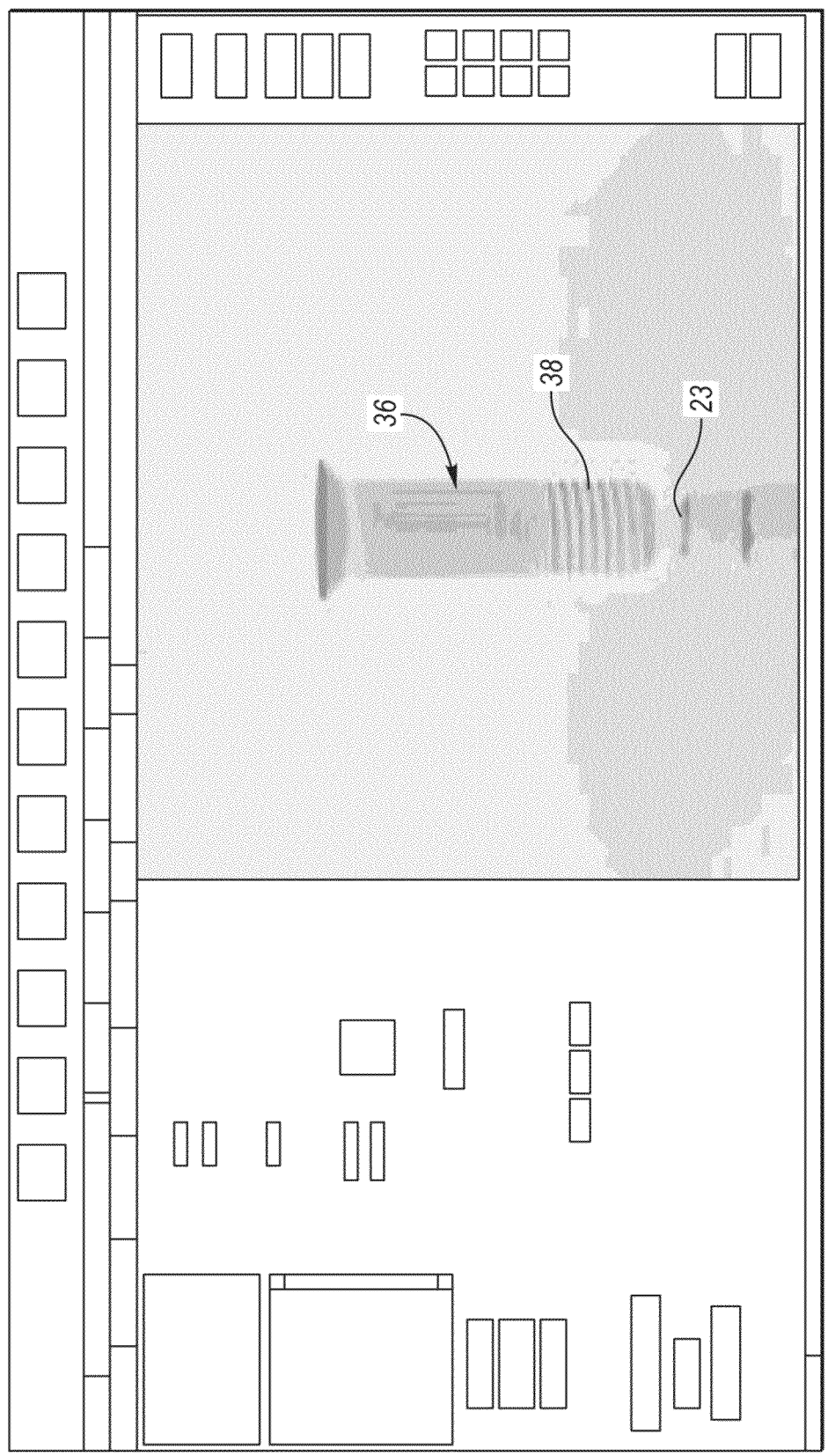
FIG. 12 is a schematic view of a screen shot (without displayed icons or data) which shows a threaded, vertically held part having no surface defects.
Figure 13:
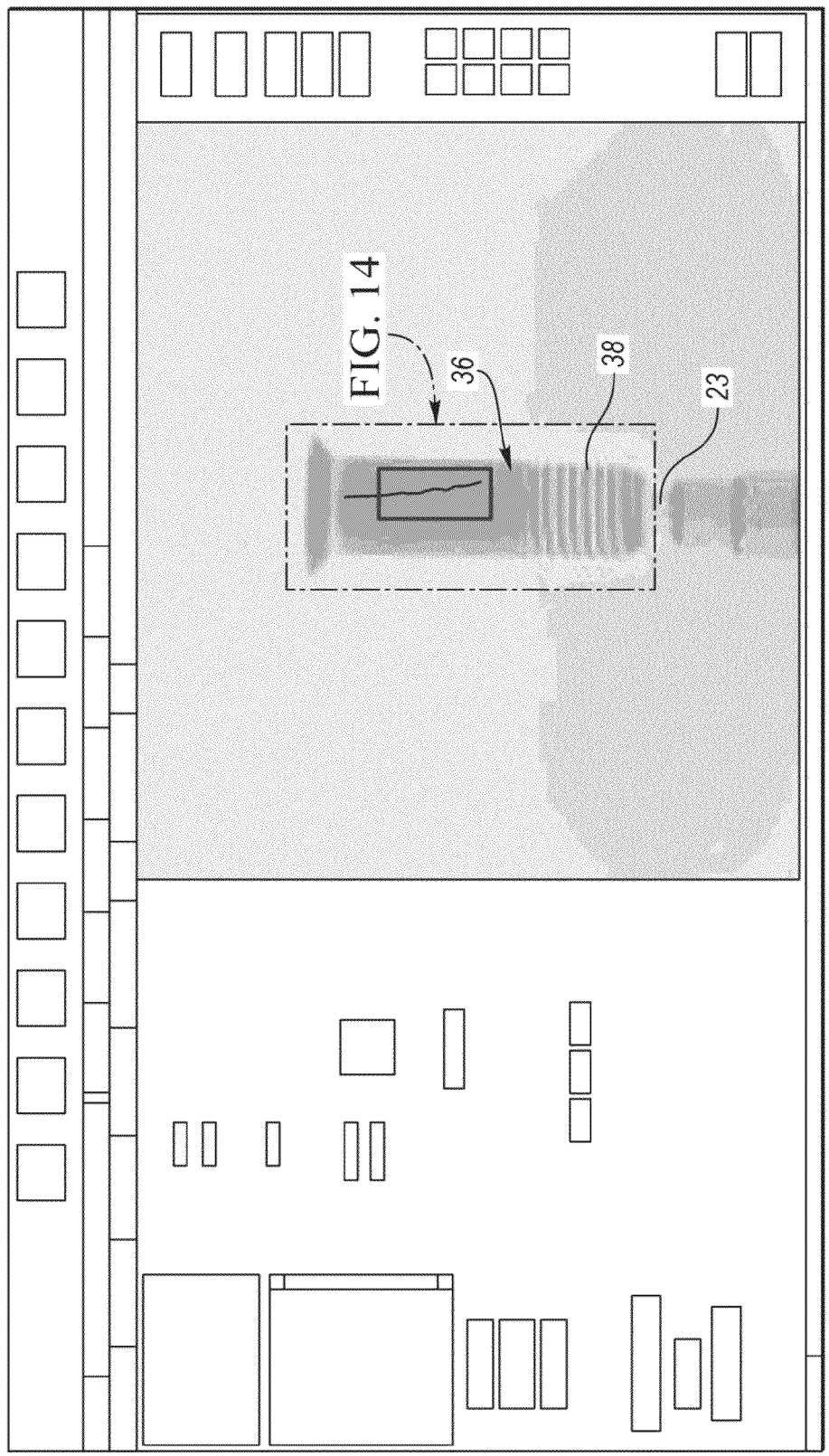
FIG. 13 is a schematic view of a screen shot (without displayed icons or data) which shows a threaded, vertically held part with a surface scratch within a solid rectangular box which, in turn, is located within a box formed by phantom lines.
Figure 14:
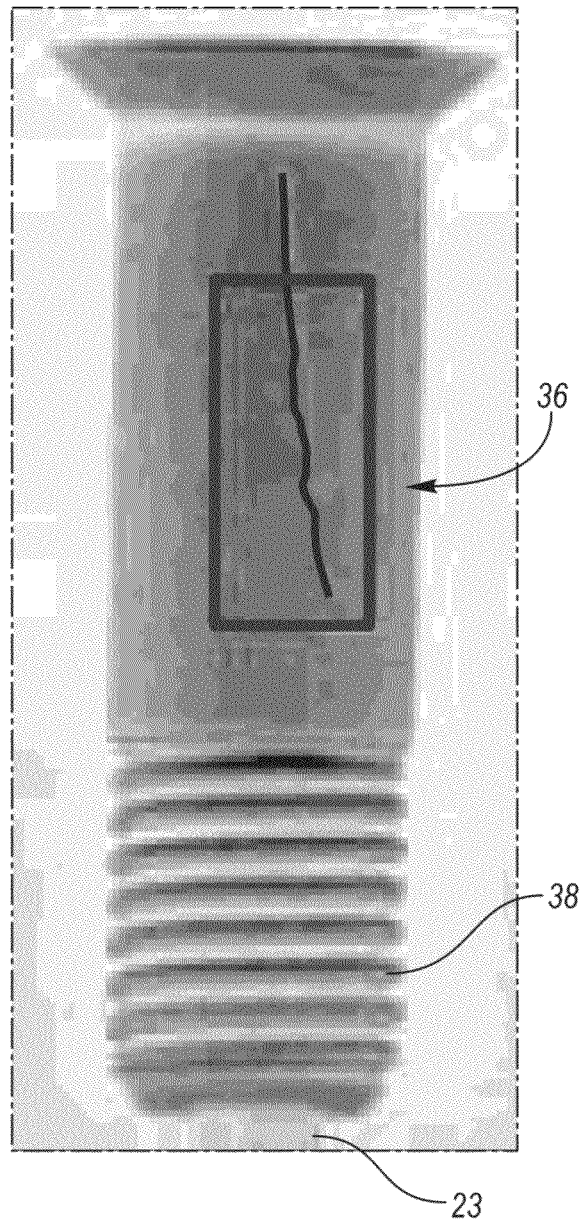
FIG. 14 is an enlarged, detailed schematic view of the part within the phantom-line box located in the screen shot of FIG. 13.

Then as shown in FIGS. 8-11 a V-block or device 35' supported on a shaft 34' with a hex end mates with the recess bit 23 or a recess bit 23' to provide end views of the part. A part whose ends are to be inspected is held horizontally by the V-block 35' between angled surfaces 33' thereof (FIGS. 9-11). While a variety of bits are shown in the drawing figures, all of the bits are given either reference number 23 or 23'. The bits may be recess bits.

The lower part or recess bit 23 is mounted for rotary movement on the part stage 14 which is mounted above a top plate 42 of a base of the system 10. The part stage 14 is coupled via a coupler to the rotary output shaft 35 of an electric actuator or motor 28 supported below the plate 42. A head 37 of a vertically supported bolt 36 is driven by the bit 23 which extends into the head 37 at one end surface thereof. The bit 23 may be an external or internal drive depending on the size and shape of the part being driven. This feature allows the threads 38 as well as the entire exterior side surfaces of the bolt 36 to be optically inspected.

Figure 1:
FIG. 1 is a top plan view of various manufactured parts including threaded parts, fasteners and cartridge cases having various symmetric and non-symmetric features and defects which can be extracted and measured using at least one embodiment of the present invention.
Figure 15:
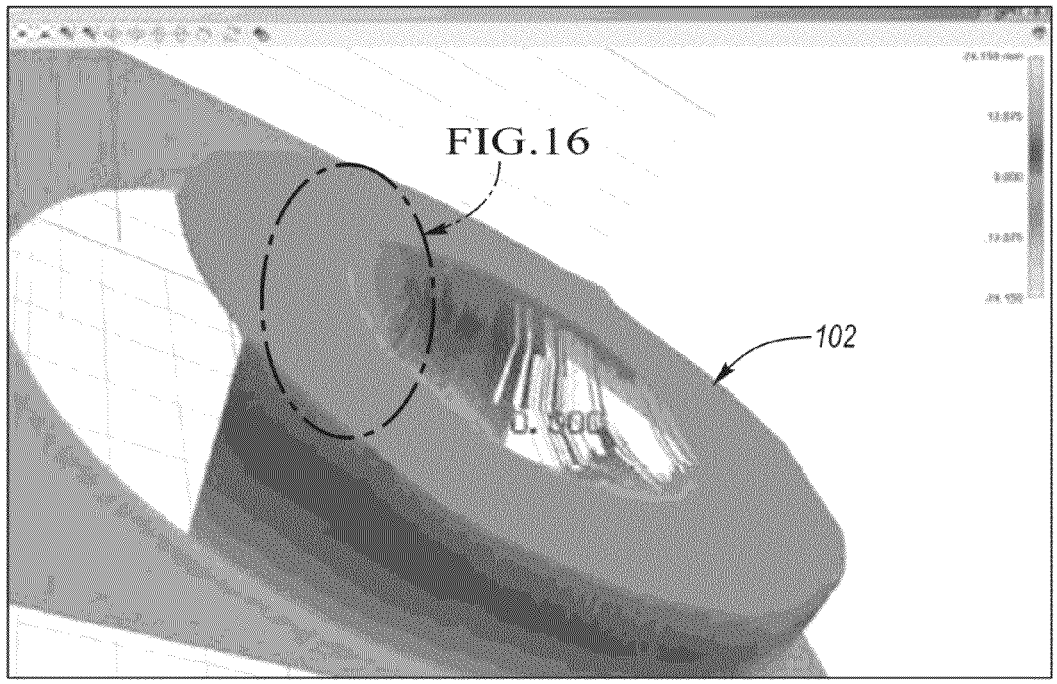
FIG. 15 is a schematic view of a screen shot which shows a laser topography image including an encircled scratch on the end surface of a part such as a valve spring retainer.
Figure 16:
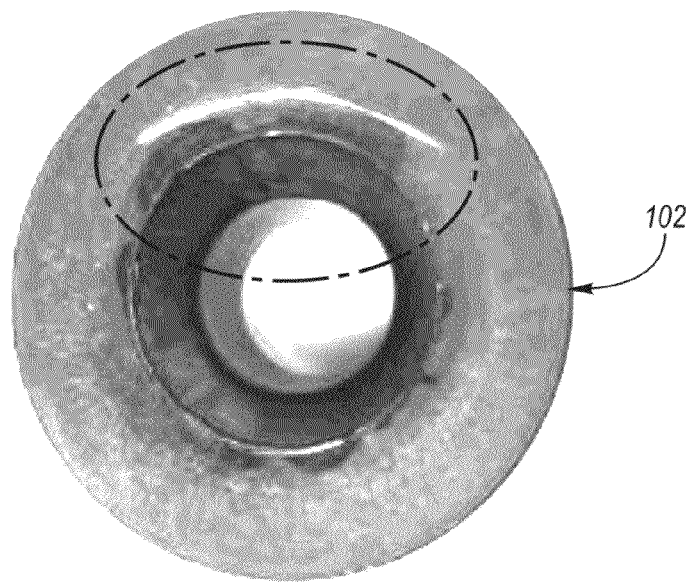
FIG. 16 is an end view of the valve spring retainer of FIG. 15 with the encircled scratch of FIG. 15.

Other parts, such as the ammunition case 100 of FIG. 1 and a valve spring retainer, generally indicated at 102 in FIGS. 15 and 16, can be rotatably driven by the motor 28 via a motor driver controlled by a system controller (FIG. 17) while being held either horizontally or vertically.

In like fashion and referring to FIG. 19, the bolt 36' is rotatably driven by an actuator or motor 28' such as an electrical motor with an encoder 15' or a stepper motor (without an encoder) via a motor driver or motor controller upon receiving control signals from a system controller. The motor 28' either directly or via a transmission coupled to the output shaft of the motor 28' may also alternatively raise or lower the fixture assembly 32' and the supported bolt 36' via a second motor driver or controller.

Figure 2:
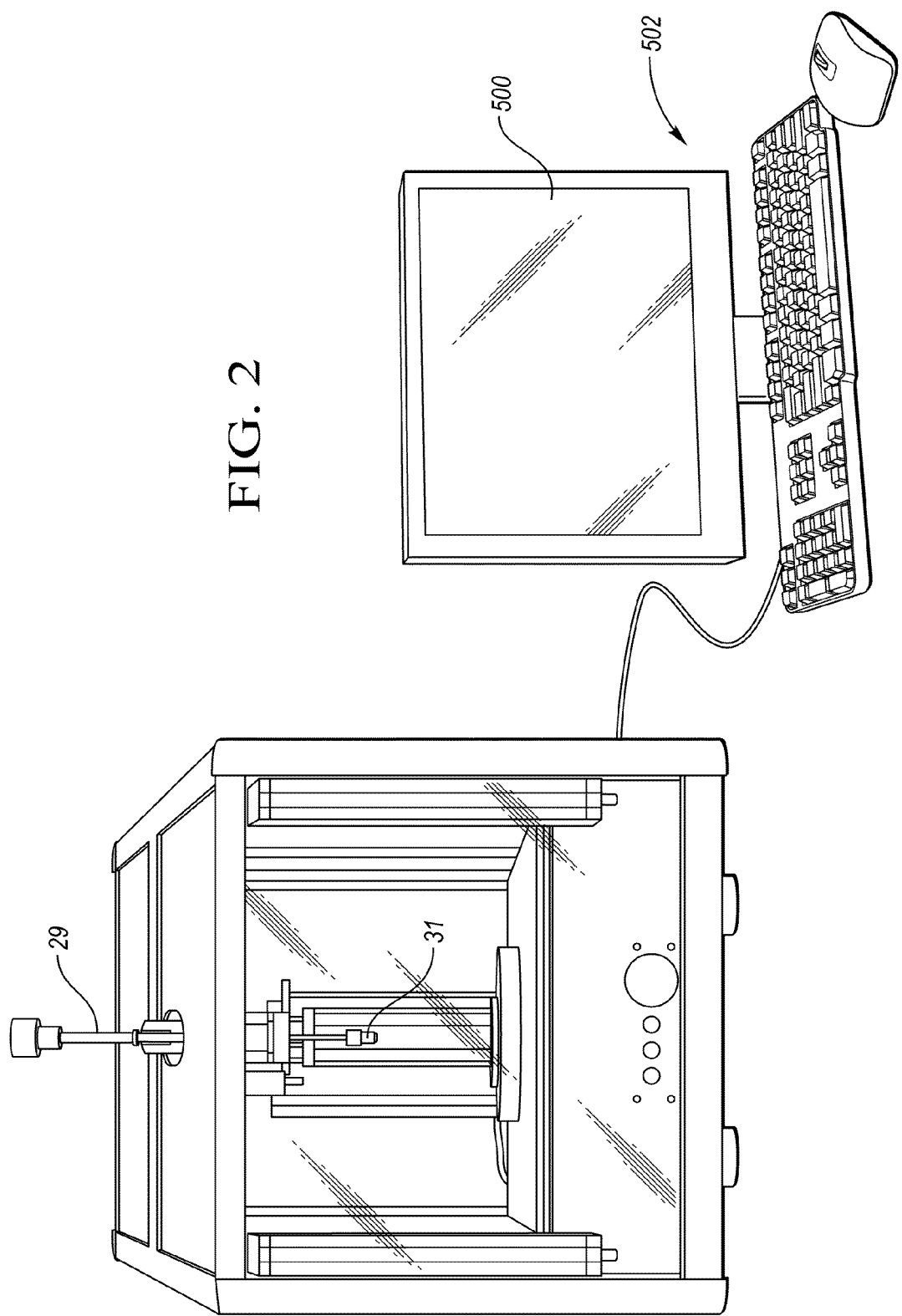
FIG. 2 is a schematic perspective view of an example embodiment of a system (including a computer subsystem and a housing or enclosure) of the present invention but without the optical inspection devices, associated electronics, and entire fixture subassembly of FIGS. 3 and 8 within the enclosure.
Figure 3:
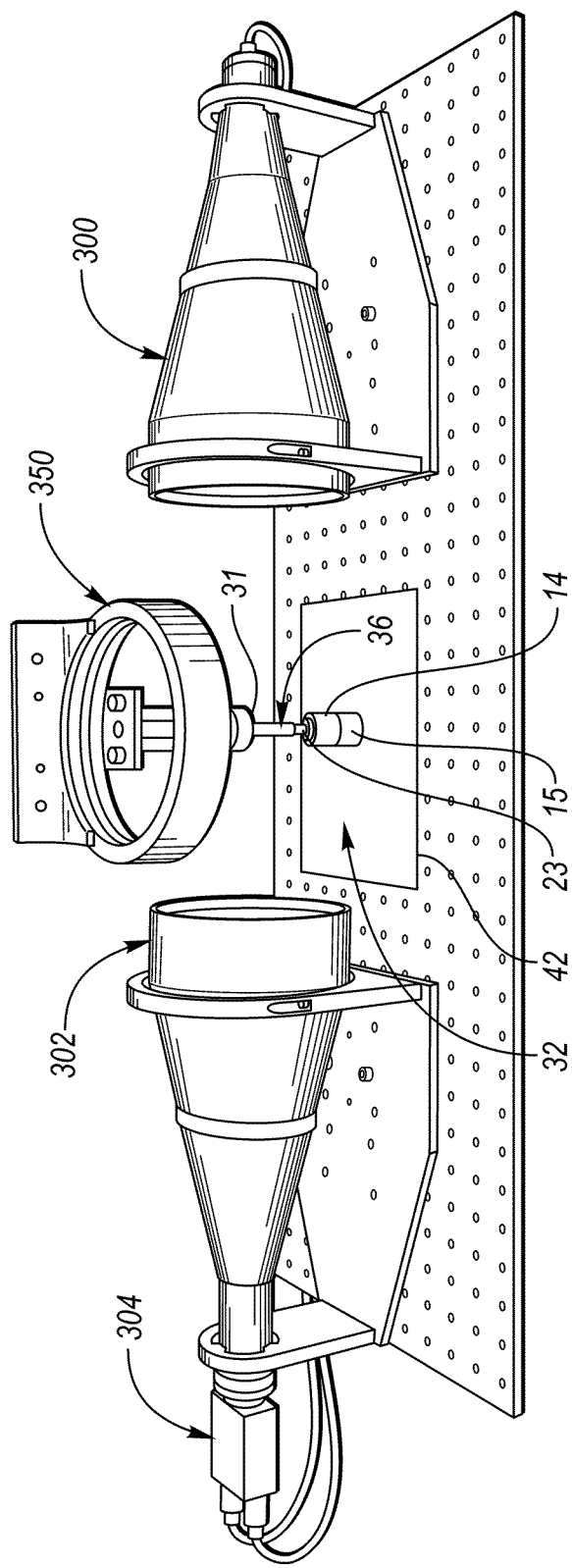
FIG. 3 is a schematic perspective view of optical inspection devices and the fixture subassembly for use in the system of FIG. 2 for viewing a part from its sides to obtain side profile views.
Figure 6:
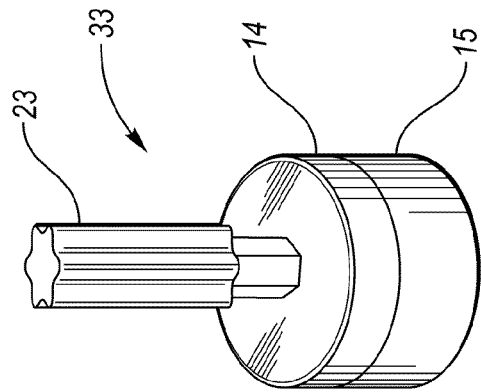
FIG. 6 is a top perspective view of a recess bit supported on a rotary stage and a rotary encoder.
Figure 5:
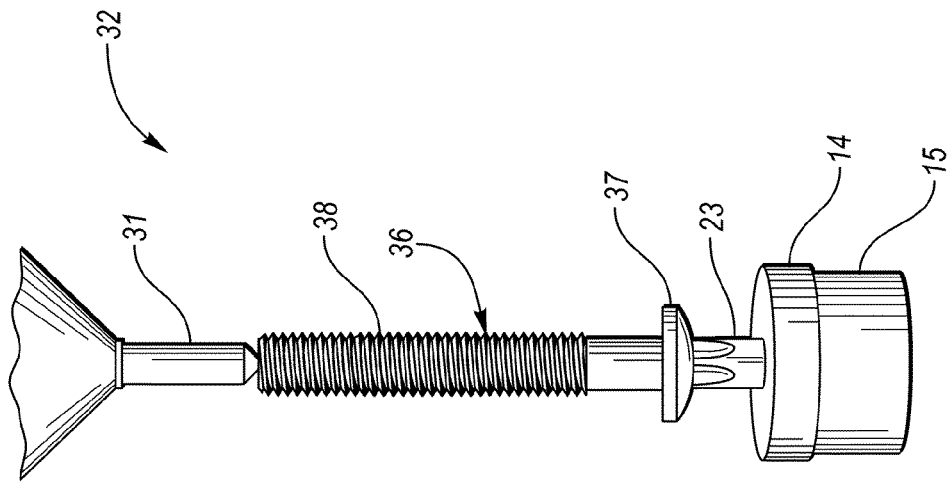
FIG. 5 is a side elevational view, partially broken away, of upper and lower fixturing components with a treaded fastener held therebetween, a rotary stage and a rotary encoder.

Referring to FIG. 2, a partial system of at least one embodiment of the present invention is shown. The upper tooling unit 31 is shown for bolts and ammunition cases. The upper tooling unit 31 includes a rod 29 which is manually movable along a central axis of the rod 31 in up and down directions by an operator of the system. The upper tooling unit 31 (as described in detail in U.S. Pat. No. 8,004,694) includes an upper part (for bolts) or an upper part (for cases) and typically comprises a spring-loaded, upper holding device or tooling assembly.

Figure 4:
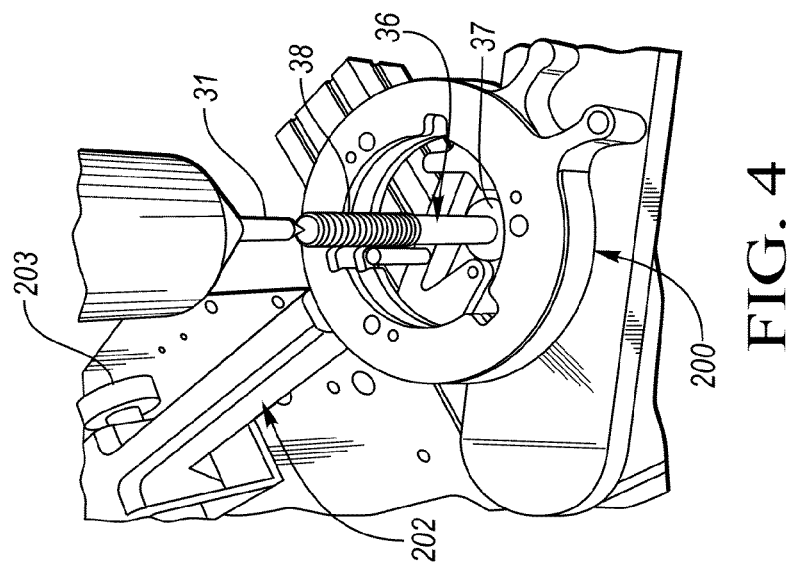
FIG. 4 is a schematic perspective view, partially broken away, of a part-centering and aligning iris or subsystem with a threaded part therein for use in the system of FIG. 2.
Figure 7:
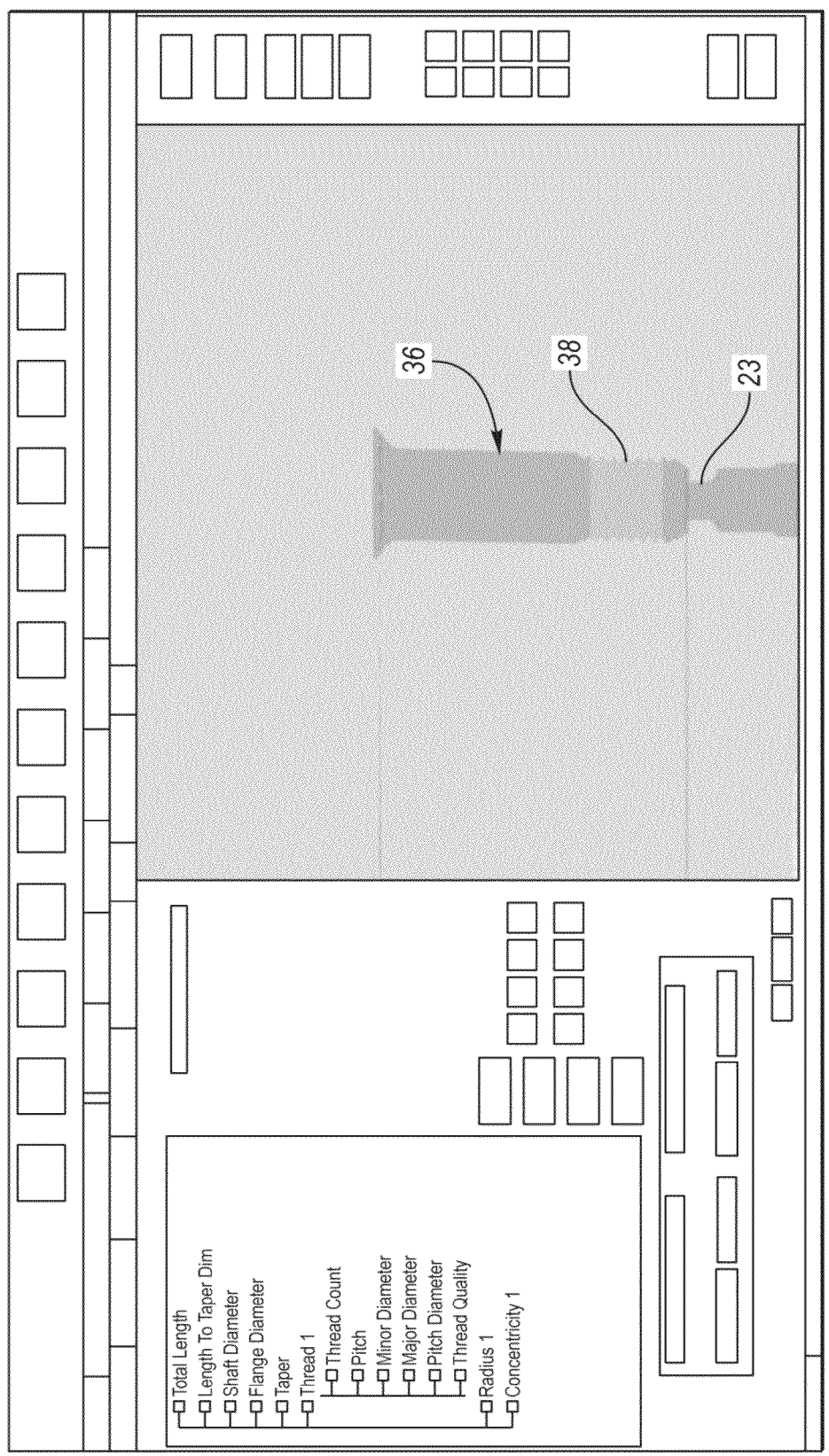
FIG. 7 is a schematic view of a screen shot (with a limited amount of data displayed therein) from a user interface of a PC which shows a profile view of a threaded fastener vertically supported by a recess bit.
Figure 8:
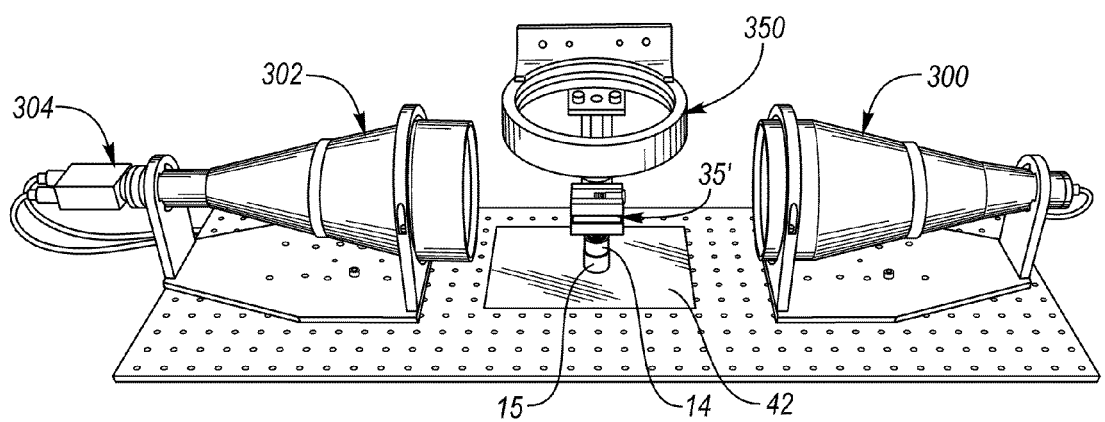
FIG. 8 is a view similar to the view of FIG. 3 but with a second fixturing component including a V-block mating with and removably connected to a recess bit for use with the same optical inspection devices of FIG. 3 to optically inspect the ends of a part horizontally held or supported by the V-block.

Referring again to FIG. 4 and as described in U.S. Pat. No. 8,550,444, the system 10 also preferably includes a part centering and aligning subsystem, generally indicated at 200. The subsystem or apparatus 200 ensures that a part is centered in the system 10 and that the part is aligned with the measurement axis (Z-axis) 13 or 13' without the need to measure any distances or angles. In other words, the apparatus 200 ensures that the part is properly placed or positioned in the system 10 prior to the part being held, for example, between the upper tooling unit and the recess bit supported on the part stage 14 or between the upper tooling unit and the V-block 35'. The part may be a manufactured part (FIG. 1) such as the threaded fastener 36 or the ammunition case 100.

As described in U.S. Pat. No. 8,550,444, the apparatus 200 includes a carrier which defines a part receiving cavity. The apparatus 200 also has a central axis substantially parallel to the measurement axis 13 or 13' or Z-axis and including a plurality of members or levers having open and closed positions. The members having holding faces which are substantially equidistant from the central axis during movement between the open and closed positions. At least one of the members applies a force on an exterior side surface of a part, disposed between the holding faces during movement between the positions to reposition the part. The repositioned part is centered and aligned with respect to the measurement axis 13 or 13'. The holding faces releasably hold the repositioned part in the holding position between the open and closed positions of the members.

The apparatus 200 also includes manually operable lever arms which are coupled to their respective relatively moveable spring-biased ring members of the carrier. Movement of one of the lever arms either towards or away from the other lever arm (depending on the biasing of the spring(s)) causes the members to move from their open position to their holding position against the part to center and align the part.

The system 10 also includes a movable stage subsystem, generally indicated at 202, coupled to the apparatus 200 for sliding the apparatus 200 relative to the repositioned part along the central or measurement axis in the open position of the members to allow the exterior side surface of the repositioned part to be measured. In turn, the slide/base unit moves the movable stage subsystem 202 up and down. A horizontal support member couples the subsystem 202 to the apparatus 200 to move the apparatus 200 along the central or measurement axis.

The system 10 further includes a mechanism which is coupled to one end of the support member for translating the support member and the apparatus 200 a limited extent relative to the subsystem 202 along the central axis. The mechanism includes a manually operable knob 203 to operate the mechanism.

Referring again to FIGS. 3, 8, 17 and 18, the system 10 also includes a backside illumination assembly, generally included at 300. The system 10' includes a backside illumination assembly, generally indicated at 300' in FIG. 19.

The illumination assembly 300 (and the assembly 300') directs a beam of collimated radiation at substantially the entire backside surface of the held part at predetermined angular increments of movement of the held part about the measurement axis of the system 10 (or system 10') during the rotational scan. The beam is occluded by the held part at each increment of movement to create a stream of unobstructed portions of the beam in rapid succession passing by and not blocked by the held part.

Preferably, substantially the entire backside surface is completely enclosed by a beam profile of the beam. The beam profile is generally rectangular with a height greater than or equal to the length of the part and a width greater than or equal to the width of the part as show in FIGS. 17 and 18.

Referring again to FIG. 19, the backside illumination assembly 300' is substantially the same as the illumination assembly 300. The assembly 300' may be movable up or down via a motor M driven or controlled by a driver/controller upon receiving a control signal from the system controller.

The illumination assembly or radiant source 300 (or assembly 300') illuminates an object such as an ammunition case or threaded bolt to be imaged, and a telecentric optical lens 302 (or lens 302' of FIG. 19) receives the radiation passing by and not blocked by the case or bolt and guides it towards an image plane of the image acquisition device or detector, generally referred as 304 (or detector 304' of FIG. 19). Consequently, the radiation source 300 (and the source 300') preferably comprises a LED emitter including a plurality of LED emitter elements serving to emit radiation in either the visible or ultraviolet range. The LED emitter of the source 300 (or source 300') is preferably high power, capable of generating 100 optical mW or more for each emitting element. A lens (not shown) collimates the radiation.

As shown in FIG. 19, the back light 300' and the detector 304' may be coupled together by a yoke 306' to rotate together about the part 36' via a motor 28' via a driver/controller upon receiving a command signal from the system controller.

An optical or optoelectronic device for the acquisition of images (for example the camera or telecamera 304 or 304') has the image plane which can be, for example, an electronic sensor (CCD, CMOS). The case, bolt or other manufactured part, is received and retained at a predetermined position and orientation for optical inspection by the fixture 32 of the system 10 (or fixture 32' of system 10'). Preferably the device 304 (and the device 304') is a high speed, high resolution digital telecamera, having an electronic sensor with individual pixels of lateral dimensions equal to or less than one or more microns.

Referring again to FIG. 19, the assembly 304' can be driven up and/or down by a motor via a driver/controller upon receiving an appropriate control signal from the system controller. Typically, movement of the assembly 304' and the backlight 300' is coordinated by the system controller so that they move in unison.

As described in the parent case of this application (U.S. Ser. No. 14/629,527), the lens 302 (and the lens 302') typically comprises a forward set of optical elements proximal to the manufactured part, a rear optical element proximal to the acquisition device and an aperture diaphragm interposed between the forward and rear sets of optical elements. The aperture diaphragm comprises a circular window transparent to the radiation, which is referred to as a diaphragm aperture. For example, the aperture diaphragm can comprise an opaque plate preferably of thickness of a few tenths of a millimeter, and the diaphragm aperture can be defined a simple hole in the plate.

The diaphragm aperture or window is coaxial to the optical axis of the forward set of optical elements, and positioned on the focal plane of the forward set defined for the wavelength range of radiation emitted by the radiant source.

The position of the focal plane of a set of optical elements mostly depends on the refraction index of the material from which the lenses are made, which, in turn, depends on the wavelength of the electromagnetic radiation passing through the lenses.

The lens 302 (and lens 302') only accepts ray cones exhibiting a main (barycentric) axis that is parallel to the optical axis of the forward set. Thereby, the lens 302 is a telecentric lens configured for the particular radiation. The rear set of optical elements serves to compensate and correct the residual chromatic dispersion generated by the forward set optical elements for the wavelength in question.

The optical axis of the rear set coincides with the optical axis of the forward set and the focal plane of the rear set defined for the wavelength cited above, coincides with the plane on which the aperture diaphragm is located. Consequently, rays of radiation conveyed by the rear set towards the image plane form light cones, the main (barycentric) axis of which is parallel to the optical axis of the lens 302 (and the lens 302').

The forward set preferably includes two positive lenses, which can exhibit a flat-convex, bi-convex, or meniscus shape. The positive lenses can both be made in common optical glass. For example, they can both be made in low chromatic dispersion crown glass, including, for example, Schott glass varieties classified with codes N-SK16, N-BK7, or B270.

The rear set of optical elements preferably comprises four lenses. The lens which is proximal to the diaphragm can be a negative lens serving to partially or completely correct the chromatic aberrations generated by the forward set. The negative lens can be bi-concave, flat-concave, or meniscus shaped, and can be made of common optical glass, for example it can be made of high chromatic dispersion flint glass, for example, Schott optical glass types classified with codes N-F2, LLF1, or N-SF1.

The three rear lenses are positive lenses that can all be made of common optical glass, for example in low chromatic dispersion crown glass, including the hereinabove cited Schott optical glass types classified with codes N-SK16, N-BK7, or B270.

The lens 302 (and the lens 302') is therefore both telecentric on the object side and telecentric on the image side, and overall the lens 302 is a bi-telecentric lens configured for light such as visible light or ultraviolet light.

Figure 17:
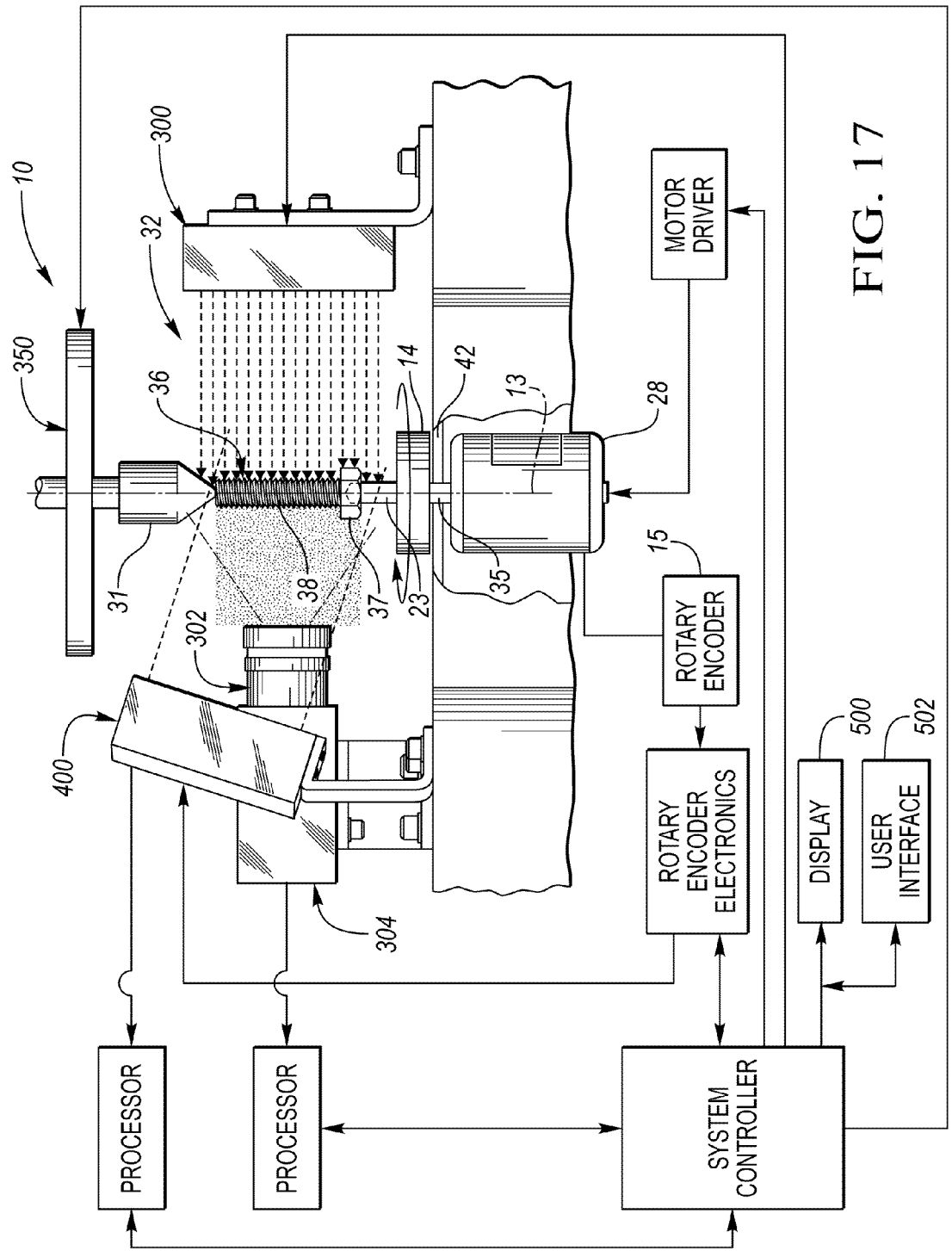
FIG. 17 is a side schematic view, partially broken away, of a system of at least one embodiment of the present invention including the optical inspection devices, actuator assembly and fixture assembly of FIG. 3 together with a block diagram of various electronics of the system, particularly showing the height of the collimated backside beam of radiation.
Figure 18:
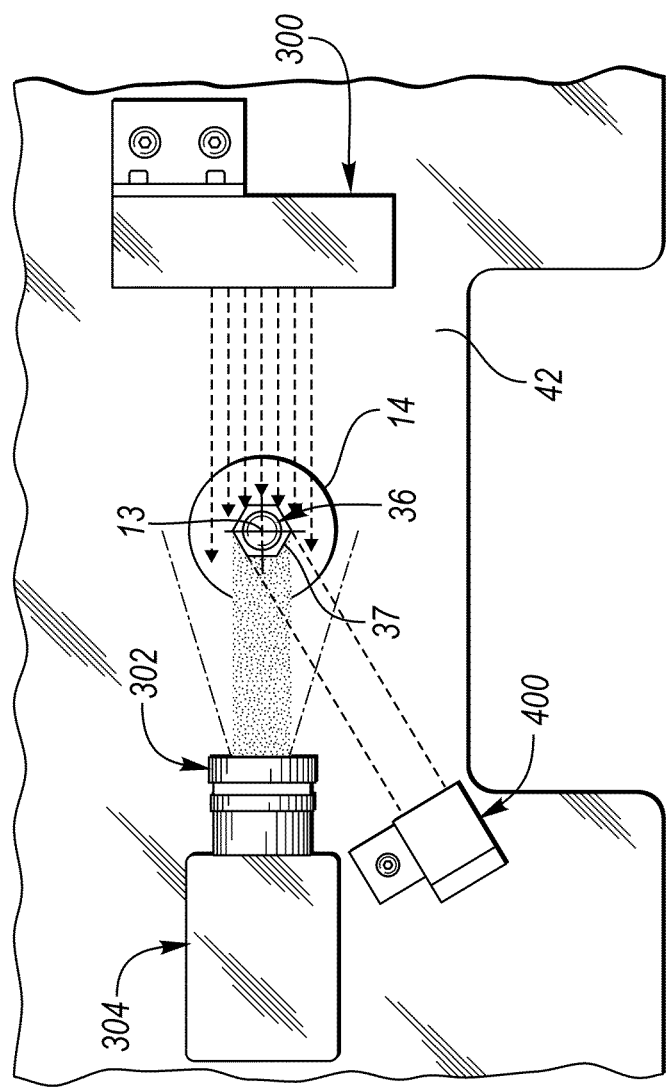
FIG. 18 is a top plan schematic view, partially broken away, of parts and devices of the system of FIGS. 3-8 and 17 particularly showing the width of the collimated backside beam of radiation.

Referring now to FIGS. 17 and 18, there is illustrated a triangulation-based sensor head, generally indicated at 400. The system 10' includes a sensor head 400' substantially the same as the sensor head 400. The sensor head 400 may comprise a high-speed, 2D/3D laser scanner (LJ-V7000 series) available from Keyence Corporation of Japan. Such a sensor head from Keyance generates a laser beam that has been expanded into a line and is reflected from the side surface of the part as well as any radially extending surfaces of the part, such as the threaded bolt 36. The reflected line of light is formed on a HSE3-CMOS sensor, and by detecting changes in the position and shape of the reflection, it is possible to measure the position of various points along the surface of the part.

Alternatively, during the scans of the side profile and the end views, a laser line may be painted on the part and a vision subsystem positioned on either side of the laser line receives reflected laser light and the resulting images provides a 3D image (including Z axis or depth). In this way, both visual defects and measurement features or characteristics that require a depth component are simultaneously extracted. FIGS. 15 and 16 show a valve spring retainer imaged by laser topography wherein scratches and depth features are imaged.

The sensor head 400' of FIG. 19 may rotate and/or linearly move via a motor via a rotary driver/controller and/or a linear driver/controller, respectively, upon receiving command signals from the system controller. A transmission (not shown) may convert the rotary motion of the motor output shaft to linear motion.

The sensor head 400 typically includes a cylindrical lens, at least one and preferably two semiconductor laser diodes, a GP64-Processor, a 2D Ernostar lens and the HSE3-CMOS Sensor. Preferably, the laser diodes emit "blue" light beams which are polarized and combined by optical elements or components to form the line of laser light.

Preferably, the beams from the pair of blue laser diodes are combined such that the transmitted beam is polarized in both X and Y axes. The captured images at the sensor in both polarizations are used to generate a resulting 2D profile signal wherein stray reflections are cancelled.

As the manufactured parts rotate corresponding sets of 2D profile signals are generated by the sensor head 400. At least one processor processes the sets of 2D profile signals to obtain a 3D view of the complete side and end surfaces and any radially extending surfaces of the part.

The system controller provides control signals based on the signals from the rotary sensor or encoder 15. Alternatively, sensor(s) and/or encoder(s) are not required if stepper motor(s) are provided. Alternatively or additionally, the signals from the rotary encoder 15 are directly utilized by the sensor head 400 at the station to control the sensor head 400. The control signals are utilized to control the sensor head 400 which preferably have encoder inputs which allow precise control over the position of 2D profile signals samples.

At least one signal processor may process the sets of 2D profile signals to identify a defective part as described in greater detail herein below. The at least one processor may process the sets of 2D profile signals to obtain one or more measurements of the part.

A comparison of such a sensor head 400 with a 3D measurement camera reveal the following:

1. Easy Installation

When using a 3D camera, the laser light source and receiver (camera) are independent of each other, greatly complicating on-site installation and adjustment. With such sensor heads 400, the laser light source and receiver are contained in a single body or enclosure, making transmitter-to-receiver mounting adjusting unnecessary. This also ensures that the transmitter and receiver maintain this alignment regardless of machine use.

2. No Linearization Required

When using a 3D camera, the height of individual pixels and pixel pitch vary due to the relative positions of the laser light source and the receiver, requiring on-site linearization following installation. With such sensor heads 400, the output data is pre-linearized by the on-board controller (not shown) of the sensor head 400 without the need for additional post-processing.

3. Out of the Box Traceability

Because each such sensor head 400 is not a machine vision camera, but a traceable measurement device, traceability and calibration documentation is available out of the box. All such devices are factory calibrated to international traceability standards and compliance documentation is readily available.

The sensor head 400 and the at least one processor can extract serrations, knurls, twelve point aerospace or non-symmetric features of part like D-head or T-head bolts etc. The operator may tell the system controller via a display 500 and user interface 502 (FIGS. 2 and 17) where the interesting parameters are located on the Z axis (height of the part). Then, the software tools extract and measure features from the images and resulting 2D profile signals created by the reflected lines of radiation.

The 2D profile signals may be processed by the at least one processor under system control to obtain a 360 degree panoramic composite view or image which is used by the processor to determine at least one of a dent, a split, a perforation, a crack, a scratch, a wrinkle, a buckle, a bulge, and a surface blemish located at the side surfaces of the part where the part is an ammunition case.

The frontside illumination device of the first embodiment may include a ring LED illuminator 350 (FIGS. 3, 8 and 17) and the frontside illumination device of the second embodiment may include a ring LED illuminator 350' (FIG. 19). Each illuminator 350 and 350' includes a curved array of LED light sources, groups of which are under control of the system controller to provide direct illumination of the front of the case or bolt and are used to enhance defects in the front surface of the case or bolt. Alternatively, the frontside illumination device may be side-mounted so that the front light comes from the side of the part and not from above the part, i.e., basically like painting a thin line along the length of the part.

The detected optical images are processed by the image processor to determine at least one of a dent, a split, a perforation, a crack, a scratch, a wrinkle, a buckle, a bulge, and a surface blemish located at the side surfaces of the case.

Data/Image Processor for the Detection of Surface Defects on Small Manufactured Parts This vision system is especially designed for the inspection of relatively small manufactured parts (i.e. the parts of FIG. 1 which typically have a diameter of 1 mm to 50 mm and a length up to 150 mm. The processing of images of the cartridge cases and like parts to detect defective cases is generally described in issued U.S. Pat. No. 7,403,872 as follows.

Dent Detection

The detection of dents relies on the alteration of the angle of reflected light caused by a surface deformation on the inspected part. Light which is incident on a surface dent will reflect along a different axis than light which is incident on a non-deformed section of circumference.

There are generally two ways to detect dents using this theory. One option is to orient the light source so that light reflected off the part exterior is aimed directly into the camera aperture. Light which reflects off a dented region will not reflect bright background. Alternatively, the light source can be positioned with a shallower angle to the part. This will result in a low background illumination level with dents appearing as well deemed origin spots on the image.

The vision system detects dents on parts with multiple tapered sections. In particular, a bright background is created in highly tapered regions (with dents appearing as dark spots) while a dim background is created in flatter regions (with dents appearing as bright spots).

As previously mentioned, the vision system has two types of lights, each of which can be independently adjusted in order to properly illuminate a given taper.

Perforation Detection

Detecting perforations uses both of the principles outlined above. The task is much simpler however, as the region containing the defect is completely non-reflective. Therefore, perforations are visible as dark spots on surfaces illuminated by either shallow or steep angle illumination.

Software

Because the part is essentially at a pre-defined location and orientation when the images are acquired, the software need not auto-locate the part and identify regions of interest using preset visual clues.

Defect detection in each region of interest is typically conducted by first running several image processing algorithms and then analyzing the resultant pixel brightness values. Groups of pixels whose brightness values exceed a preset threshold are flagged as a "bright defect," while groups of pixels whose brightness values lie below a preset threshold are flagged as a "dark defect." Different image processing techniques and threshold values are often needed to inspect for bright and dark defects, even within the same part region.

Part Location

Previously locating the part in the image may be accomplished by running a series of linear edge detection algorithms. This algorithm uses variable threshold, smoothing and size settings to determine the boundary between a light and dark region along a defined line. These three variables are not generally available to the user, but are hardcoded into the software, as the only time they will generally need to change is in the event of large scale lighting adjustments.

The software first uses the above edge detection algorithm to find the back (left) end of the part in the image.

Once the left edge of the part has been located, the software runs four more edge searches along the top and bottom edges of the part.

Once the top and bottom edges of the part have been located, the midpoints of the edge pairs are calculated and joined in order to find the centerline.

The centerline search is then performed again, but rather than conducting the linear edge detections in the vertical direction, they are conducted perpendicular to the newly found centerline. This iteration reduces the small angle error associated with any potential misalignment of the part in the field of view.

A new centerline found using the results of the repeated top and bottom edge search.

Finally, the left edge is again located, this time along the new centerline. This action locates the very center of the left-hand edge of the part.

Part Regions

Once the part has been located in the image, a framework of part regions is defined using a hard-coded model of the anticipated part shape. In the case of ammunition, the regions defined by the framework include head, extractor groove, case, taper, and neck. Each of these regions can be varied in length and width through the user interface in order to adapt the software to varying case sizes. Note that although regions can be adjusted in size, they cannot have their bulk shape changed. A checkbox allows the taper and neck regions to be removed in order to inspect pistol cases (which do not have a taper). The size of the region framework as well as the state of the Taper/No-Taper checkbox is saved in the part profile.

Defect Search

Once the case regions have been defined, a buffer distance is applied to the inside edges of each region. These buffered regions define the area within which the defect searches will be conducted. By buffering the inspection regions, edge anomalies and non-ideal lighting frequently found near the boundaries are ignored. The size of the buffers can be independently adjusted for each region as part of the standard user interface and is saved in the part profile.

There are two general defect detection algorithms that can be conducted in each region. These two algorithms are closely tied to the detection of dents and perforations respectively as discussed above in the lighting section. More generally however, they correspond to the recognition of a group of dark pixels on a bright background or a group of bright pixels on a dark background.

Although there are only two defect detection algorithms used across all the regions on the part, the parameters associated with the algorithm can be modified from region to region. Additionally, the detection of dark and/or bright defects can be disabled for specific regions. This information is saved in the part profile.

Dark Defects

The detection of dark defects is a 6 step process.

1. Logarithm: Each, pixel brightness value (0-255) is replaced with the log of its brightness value. This serves to expand the brightness values of darker regions while compressing the values of brighter regions, thereby making it easier to find dark defects on a dim background.

2. Sobel Magnitude Operator: The Sobel Operator is the derivative of the image. Therefore, the Sobel Magnitude is shown below:

$$S_M = \sqrt{\left(\frac{\partial f}{\partial x}\right)^2 + \left(\frac{\partial f}{\partial y}\right)^2}$$

although it is frequently approximated as the following:

$$S_M = \frac{\frac{\partial f}{\partial x} + \frac{\partial f}{\partial y}}{2}$$

The Sobel Magnitude Operator highlights pixels according to the difference between their brightness and the brightness of their neighbors. Since this operator is performed after the Logarithm filter applied in step 1, the resulting image will emphasize dark pockets on an otherwise dim background. After the Sobel Magnitude Operator is applied, the image will contain a number of bright 'rings' around the identified dark defects.

3. Invert Original Image: The original image captured by the camera is inverted so that bright pixels appear dark and dark pixels appear bright. This results in an image with dark defect areas appearing as bright spots.

4. Multiplication: the image obtained after step 2 is multiplied with the image obtained after step 3. Multiplication of two images like this is functionally equivalent to performing an AND operation on them. Only pixels which appear bright in the resultant image. In this case, the multiplication of these two images will result in the highlighting of the rings found in step two, but only if these rings surround a dark spot.

5. Threshold: All pixels with a brightness below a specified value are set to OFF while all pixels greater than or equal to the specified value are set to ON.

6. Fill in Holes: The image obtained after the completion of steps 1-5 appears as a series of ON-pixel rings. The final step is to fill in all enclosed contours with ON pixels.

After completing these steps, the resultant image should consist of a pixels corresponding to potential defects. These bright blobs are superimposed on areas that originally contained dark defects.

The detection of bright defects is a two-step process.

1. Threshold: A pixel brightness threshold filter may be applied to pick out all saturated pixels (greyscale 255). A user-definable threshold may be provided so values lower than 255 can be detected.

2. Count Filter: A count filter is a technique for filtering small pixel noise. A size parameter is set (2, 3, 4, etc.) and a square box is constructed whose sides are this number of pixels in length. Therefore, if the size parameter is set to 3, the box will be 3 pixels by 3 pixels. This box is then centered on every pixel picked out by the threshold filter applied in step 1.

The filter then counts the number of additional pixels contained within the box which have been flagged by the threshold filter and verifies that there is at least one other saturated pixel present. Any pixel which fails this test has its brightness set to 0. The effect of this filter operation is to blank out isolated noise pixels.

Once these two steps have been completed, the resultant binary image will consist of ON pixels corresponding to potential defects. Furthermore, any "speckling" type noise in the original image which would have results in an ON pixel will have been eliminated leaving only those pixels which are in close proximity to other pixels which are ON.

Pixel Count

After bright and/or dark defect detection algorithms have been run in a given region, the resultant processed images are binary. These two images are then OR'ed together. This results in a single image with both bright and dark defects.

The software now counts the number of ON pixels in each detected defect. Finally, the part will be flagged as defective if either the quantity of defect pixels within a given connected region is above a user-defined threshold, or if the total quantity of defect pixels across the entire part is above a user-defined threshold.

Thread Signal/Data Processing

Introduction

What follows is a description of a thread parameter estimation process. This process which is described in general in published U.S. patent application 2010/0238435 provides one embodiment of a standard thread measurement "feature" in the method and system of the invention.

Thread Signal Processing

Thread signal processing is the process of estimating the following thread parameters.

1) pitch
2) major diameter
3) minor diameter
4) functional diameter
5) lead deviation
6) pitch diameter As the thread signal processing proceeds, a number of intermediate data products are produced in early processing stages that are further analyzed in later stages. These include:

rough pos/neg crossing locations
rough crest locations
wire position search intervals
left/right flank lines
wire positions
precise crest/root locations
3-crest average/median measurements of major diameter, minor diameter, pitch diameter
3-D crest cylinder axis
wire position projections on the 3-D crest cylinder axis
3-D crest cylinder diameter
3-D crest root-mean-square distance between crest data and fit.

These intermediate data products are analyzed to produce final estimates of the thread parameters. For example major diameter is estimated as twice the radius of the 3-D crest cylinder. The 3-D crest cylinder axis then depends on the precise crest/root locations. The crest/root locations then depend on the search intervals based on rough crest locations and pos/neg crossings, and on data from the original calibrated part data.

Processing Restrictions

Inspection Region

The thread processing occurs between position limits called an inspection region. In template editor, the user specifies the inspection region by manipulating the upper and lower stage position limits, overlaid on an image of the part.

These limits utilize the calibrated sensor position so that measurements by are aligned to the approximately similar physical positions on the part.

The estimation of thread parameters is specified to be an average estimate over all the data within which the inspection region. In practice, some of the intermediate data products are estimated outside of the inspection region in order to allow estimation of all thread parameters within the full region. For example, a wire position within the inspection region may require a thread crest outside the inspection region.

Measurement Assumption for the Inspection Region

The following requirements guide the user's placement of the inspection region on the image of the part.

The first assumption is that the thread parameters be constant throughout the inspection region. This enables the software to average the estimates from different positions within the inspection region and not be concerned with partitioning or segmenting the data into different regions for special processing.

This requirement excludes the following types of data from the inspection region:

the beginning or end of a threaded region, with thread crests less than full height.
a threaded region with a taper.
a threaded region with a notch or extensive damage.

A second assumption is that the inspection region contains at least 4-6 thread pitches. This amount of data is required to construct several of the intermediate data products with the required accuracy.

A third assumption is that the thread be manufactured with a 60-degree flank angle. Thread processing implicitly utilizes this parameter in several places. One of the most direct usages is the conversion of lead deviation into functional diameter.

A fourth assumption is that the thread has a cylindrical cross section. Non-cylindrical threads would require the 3-D peak cylinder to be suitably generalized. Incorrect fit to a non-cylindrical cross section would lead to incorrect lead deviation measures.

A fifth assumption is that the thread has a single helix.

Measurement of the following threaded fasteners are provided:

non-standard thread types, especially self-tapping screws,
small threaded regions with 2 or 3 pitches.
Taptite trilobe threaded regions.

Rough Crossings

The thread model describes herein below is a sampled representation of one thread profile, for exactly one pitch. Thread model starts at the midpoint of a rising thread flank and ends one pitch later.

Using a correlation detector the thread model is matched to data within the inspection regions producing thresholded detections within the inspection region, that are called crossings.

"Refinements" noted herein may make the crossings more accurate. The refinements also separate the crossings into positive crossings and negative crossings. The thread model is a lateral sequence of points that represent a best estimate of the outline of one cycle of the thread form.

Rough Crest and Root Positions

A crest/root detector extracts rough crest and root positions between the matched adjacent pairs of positive and negative crossings.

Pitch Estimate

A pitch estimate is required for step set gage wire diameter. The estimate is required to be accurate enough to unambiguously select a unique gage wire from the set appropriate for the measurement. The current process utilizes a two-stage process.

This process may be simplified as described herein.

First Estimate.

Crossing data is analyzed and averaged over all sensors to create a thread pitch estimate, the "crossing pitch."

Second Pitch Estimate

The steps set wire gage diameter, wire position search intervals, measure flank lines and measure 3-point diameters noted herein below are completed in a first iteration. Then the wire positions are averaged over all sensors and positions to compute a pitch estimate.

Set Gage Wire Diameter

Gage wires are utilized in physical thread measurements of pitch diameter in the prior art. Two wires are placed in adjacent threads on one side of the part, and a single wire is placed on the other side of the part. A micrometer measures the distance between the reference line established by the two adjacent gage wires and the reference point established by the other gage wire. A tabulated correction formula converts the micrometer distance to an estimate of the pitch diameter.

Gage wire sizes are thus selected prior to the thread measurement. To do this one estimates the thread pitch as previously described and then one selects the closest gage wire in a set to the pitch estimate. The gage wire set utilized is the one appropriate to the type of measurement; currently there is one set for the metric coarse thread sequence, and another for a similar English thread set. The gage wire sets are chosen at part template edit time by making a selection in a pull down list.

Wire Position Search Intervals

One places "virtual" gage wires onto the calibrated sensor data throughout the inspection region. In order to place the "virtual" gage wires we must identify search intervals for each wire to be located.

A requirement of the following processing steps is that the wire positions in the inspection region have no gaps. Another requirement is that a wire position search interval consist of two valid thread crests, one valid thread root between the two thread crests, and valid positive/negative crossings between the crest/root pairs.

One then searches the set of positive/negative crossings and crest/root positions for the set of wire position search intervals to analyze. The result of intervals, one set per sensor.

Measure Flank Lines

For a left flank all data is analyzed between the rough positions of the left crest and the central root. One then determines the height limits of a flank line data extraction region that covers 70% (a configurable parameter) of the height interval between left crest and central root. This data is extracted into a data set and fit to a line, becoming the left flank line.

The procedure avoids the non-linear regions near the left crest and central root. In addition, a "flank line valid" flag is computed, based on the RMS distance between the left flank line and the data within the left flank line data extraction region. If the RMS distance between the flank line and the data points in the flank line data extraction interval is larger than 10 pm per point (a configurable parameter), then the flag is set to invalid.

The process is repeated for the right flank line and then for all wire position search intervals.

Measure Wire Positions

The wire positions are calculated, given the left and right flank lines and the wire size. The virtual wire is tangent to each flank line and the resulting position is calculated with a simple geometric formula.

The position has a valid flag that is true when both flank lines are valid and false otherwise.

Measure 3-Point Diameters

The 3-point technique is a method to measure the minor, major, and pitch diameters without explicitly utilizing 3-D information.

For example, consider the major diameter. It is defined as the diameter of a cylinder that contains all the inspection region's thread crests.

In this method, the top of a thread crest in calibrated sensor coordinates forms an elementary measurement. The elementary measurements are combined into triplets for further analysis. Only crests from the two sensors of a single laser are combined.

Two adjacent thread crest positions are combined with the thread crest position that is closest to the average position of crests. The two crests form a reference line. Then the distance from the reference line to the crest is computed. This is the 3 crest distance for that crest triplet.

In this manner, the 3-crest distances from all adjacent crest triplets are computed. The 3-crest distances are all added to a data vector. The 3-crest diameter measurement is either the average or the median of all the 3-crest distances within the 3-crest data vector.

3-Point Minor Diameter

The 3-point minor diameter computes 3-point distances using precise root locations in the sensor data. The 3-point minor diameter is the average of the 3-point distance vector.

3-Point Major Diameter

The 3-point major diameter computes 3-crest distances using precise crest locations in the sensor data. The 3-point major diameter is the median of the 3-point distance vector.

3-Point Wire Pitch Diameter

The 3-point pitch diameter computes 3-point distances using the wire positions computed in the sensor data. The 3-point wire pitch diameter is the median of the 3-pointwire pitch diameter.

Measure 3-D Crest Cylinder

The measured thread crest position data is analyzed to obtain a 3-D cylinder with least squares methods. The 3-D crest cylinder fit has several output parameters of interest.

the RMS distance between the crest position data and the fitted shape.

the 3-D location of the cylinder's central axis.

the radius of the cylinder

Project Wire Positions onto 3-D Crest Cylinder Axis

Measured wire positions can be combined with the 3-D location of the 3-D crest cylinder's central axis. An imaginary disk, perpendicular to the cylinder axis that goes through the measured wire position marks a position on the 3-D crest cylinder axis.

A data set consisting of the projections of all sensor wire positions is constructed.

The output intermediate data is a vector, sorted from minimum to maximum sensor stage position of the projected wire positions.

Thread Parameter Estimation

Thread parameter estimation utilizes the intermediate data products and may also correct them based on a model of the measurement, prior to producing a final thread parameter estimate.

Wire Pitch

Thread pitch is estimated from the wire center intermediate data. For each sensor data set the adjacent pairs of wire positions are used to calculate an adjacent wire pitch, one per adjacent wire positions. For all lasers, each wire pitch is added to a wire pitch vector.

The wire pitch estimate is the median of the elements in the wire pitch vector.

Major Diameter

Thread major diameter is typically reported as the diameter of the 3-D crest cylinder.

If the 3-D crest cylinder fit was unsuccessful, the major diameter is estimated in a different way, detailed below. The cylinder fit can fail due to several factors listed here:

part inclined at too great an angle with respect to the stage axis.

thread crest positions do not fit a cylinder, the RMS fit-to-data distance is too large.

When the cylinder fit fails the major diameter is estimated from the 3-point major diameter data. This case is special because a previous condition (cylinder fit) has already failed. In practice, the cylinder fit most often failed when the threaded region was too short or the inspection extended beyond the end of the threaded region.

Because of this bias a simple median of the 3-point major diameter data would typically be too low, most of the good 3-point data was concentrated at the highest measurements. In this case the major diameter estimate is the value such that 20% of the 3-point data is higher and 80% of the 3-point data is lower.

Calibration Correction

Major diameter is also corrected by a final end-to end calibration of the total system. The reported major diameter is often two low, with bias ranging from −20 μm to 0.

After diameter calibration the system is exposed to a set of measured thread plug gages. One then plots their major diameter bias as a function of diameter and fit a simple segmented line to the bias results. These bias fits then are entered into the system configuration file and are used to correct the measured major diameter with the measured bias.

Minor Diameter

Thread minor diameter is estimated with the 3-point minor diameter distance vector. The minor diameter value is the average of the elements in the distance vector.

Pitch Diameter

Pitch diameter estimation uses two sets of intermediate data products, the wire positions and the 3-D crest cylinder fit.

The pitch diameter estimate calculation is presented in a step-by-step list below:

a) Compute the pitch diameter contact points with the thread flanks by calculating the intersection of the wire shape with the left or right flank lines.

b) Average the left and right points of intersection, and compute the distance (radius) from the average point to the 3-D crest cylinder fit axis. This is the pitch diameter radius for each wire position.

c) Calculate the average value of the pitch diameter radius.

d) Correct each average wire position radius for the part projection angle, using the angle of the 3-D crest cylinder axis to the stage axis, projected into the sensor's coordinate system.

e) Add left and right sensor corrected pitch diameter radius estimates to product an estimate of the pitch diameter for each view.

f) Average the laser estimates to produce the system pitch diameter estimate.

Correction for Part Projection Angle

The computation of pitch diameter is complicated by projection effects. The light performs an almost perfect orthographic (shadow) projection of the thread's shape. However, the projection is not the same thing as the thread cross section, which is specified in thread design documents. The cross section is the thread shape if it were cut by a plane going through the thread's central axis.

The difference is caused by the thread lead angle, which is in the range of 1-3 degrees for many typical threads. The lead angle means that the thread cross section is most accurately viewed in shadow when the viewing direction coincides with the direction of the lead.

It is impossible to position the thread so that a shadow view of the thread is simultaneously aligned with the top and bottom threads. For the example of a thread with a 3 degree lead angle, tilting the thread to align the top of the thread with the viewing angle will make the angle between the lead and the viewing angle for the bottom thread about 6 degrees.

A correction factor was developed for this effect. If one knows to tilt of the thread with respect to the viewing angle then you can correct the observed pitch diameter radius for the expected bias caused by the projection angle. This correction is precomputed and stored in a table.

For each view the tilt of the thread with respect to the viewing angle can be obtained from the 3-D cylinder fit axis. Separate corrections are applied for the different views.

Calibration Correction

Pitch diameter is also corrected by a final end-to-end calibration of the total system. The reported pitch diameter is often too high, with bias ranging from +5 μm to +35 μm.

After diameter calibration, one exposes the system to a set of measured thread plugs gages. One then plots their pitch diameter bias as a function of diameter and fit a simple segmented line to the bias results. These bias fits then are entered into the system calibration file and are used to correct the measured pitch diameter with the measured bias.

Lead Deviation

The lead deviation estimate uses the wire pitch and the locations of the wire positions as projected onto the 3-D cylinder fit axis.

For an ideal helical thread, the wire position projections should result in a regular pattern along the 3-D cylinder fit axis. Lead deviation is the deviation of that pattern from the ideal, measured as a maximum distance of any projected wire position from the ideal pattern.

The computation of the lead deviation estimate follows a step-by-step procedure:

a) Create a wire position projection vector, containing all the data.

b) Sort the wire position projection vector in order of position along the 3-D cylinder fit axis.

c) Convert the wire positions of the elements of the vector into degrees, by multiplying by the factor (360/pitch) and then reducing the element values modulo 360.

d) Calculate an offset value so that the maximum absolute value of the degree-valued element positions is minimal. For example with a lead deviation of 0.010 mm for a 1 mm pitch thread, the absolute value of at least one degree value element position would be 3.60 degrees (0.010) mm/1 mm equals (1/100) and 360/100 is 3.60)

Convert the value from degrees to mm and report as the lead deviation estimate.

All lead deviation estimates are positive.

Calibration Correction

Errors in measurement mean that the physical measurement of a perfect thread will have a positive lead deviation.

To attempt to correct for this effect, one measures the lead deviation for a set of thread plug gages and plotted them as a function of gage diameter. The most common form observed is a constant lead deviation of 0.010 mm to 0.20 mill.

This value observed in calibration with thread gages is taken to be a bias. This amount of bias is entered into the system calibration file and used to correct the measured lead deviation for this measurement bias.

Functional Diameter

Functional diameter is currently defined in practice by the fit of a special fit gage over the thread. The special fit gage is essentially a nut that is split in two by a plane cut through the central axis of the nut. The two halves of the fit gage are held in a fixture that measures the distance between the two halves. There is one special fit gage for every thread type.

Functional diameter is defined as the pitch diameter when the special fit gage is clamped tightly over a thread plug setting gage. When one puts a different part into the fit gage the fit gage may expand slightly, due to a summation of effects involving the differences between the part and the thread plug setting gage used to setup the functional diameter measurement. The functional diameter measurement is then the thread plug setting gage's pitch diameter plus the additional separation between the two fit gage pieces.

Functional Diameter Estimator

The functional diameter measurement method is an approximation of the fit gage method. A full 3-D analog of the physical fit gage is not performed. Instead an approximation is made that involves the use of lead deviation and the shape of the thread form If the thread form is assumed to be perfect and also having a 60 degree flank angle then lead deviations should cause the thread form fit gage pieces to move apart. A single lead deviation either up or down the thread form axis will cause a single split piece of the fitting gage to move outward. The amount of outward movement for a 60 degree flank angle will be equal to (V) (lead deviation). The movement provides a clearance for both positive and negative movements of the lead, relative to a perfect helical shape.

$$FD = PD + \sqrt{3}(\text{Lead Deviation})$$

Learning the Thread Model

The thread model is a learned sequence of points that represent a best estimate of the outline of one cycle of the thread form. The thread model is calculated when the inspection region is specified, at template edit time.

The measure template routine uses a pattern match algorithm with a sine wave pattern to identify periodically in the inspection region data. This process determines an approximate thread pitch. The process also calculates a starting point in the data vector for the first beginning of the matched pattern, which is an approximation to the first midpoint of a right flank line.

With the pitch and the starting point in hand, the measure template routine can then calculate an average thread model. Starting with the first sample point in the matched pattern, points that are 1, 2, 3, . . . , N pitches later in the inspection region are averaged to form the first point of the thread model. The process is repeated for all the rest of the points in the first matched pattern. The thread model is then stored in the template for later use.

In view of the above, different embodiments of the method and system of the present invention have the following inspection capabilities:

Diameters
Tapers
Lengths
Concentricity
Hex Across Corners/Flats
Straightness
Radii
Wrench Height
Length from specified diameter
Diameter from specified length position
First Full/Last Full Thread
First Scrath/Last Scrath
Recess Depth
Parallelism/Perpendicularity
Total Indicated Run out
Theoretical Intersection
Formula Feature
Laser Topography Characteristics
O-ring groove
Undercut
Spline/Serration Characteristics
Recess Depth
Bores—Internal Diameters and Internal Hex—flats/corners
Front-Lit Characteristics
Lead Stamp Verification
Thread Lap Detection
Seams
Cracks
Visual Defects
Threads
Pitch
Pitch Diameter
Major Diameter
Minor Diameter
Functional Size
Lead Deviation
Flank Angle
Lead Angle
Root Radius
Asymmetric Threads
NPT Threads
Taptite Threaded/Blanks
C
D
E
K At least one embodiment of the method and system of the invention:

Is very affordable

Has the ability to see depth features—such as twelve point heads, splines, undercuts, bores and recess characteristics (hex flats/corners and depth)

Has improved precision and less sensitivity to fixturing

Detects Visual Defects

Generates End Views—recesses, head stamp, internal hex, bores, etc.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of optically inspecting the ends of a manufactured part at a single inspection station having a measurement axis, the method comprising the steps of:
  holding the part in a generally horizontal orientation in a fixturing assembly having a rotatable first fixturing component and a rotatable second fixturing component rotatably connected to the first fixturing component to transmit torque from the first fixturing component to the second fixturing component, the part having opposite top and bottom ends with top and bottom end surfaces, respectively, a length between the ends, a width and a part axis;
  rotating the horizontally held part about the measurement axis by an actuator assembly so that the part moves between first and second angular positions when the second fixturing component is connected to the first fixturing component;
  directing a beam of radiation from an illuminating device at the top end surface of the horizontally held part at the first angular position and at the bottom end surface of the horizontally held part at the second angular position to obtain first and second reflected beams, respectively;
  imaging and detecting the first and second reflected beams by a lens and detector assembly at the inspection station to obtain electrical signals; and
  processing the electrical signals to determine at least one geometric dimension or any visual defects at the ends of the part.

2. The method as claimed in claim 1, wherein the first and second reflected beams are detected at a single image plane.

3. The method as claimed in claim 2, wherein the image plane has a predetermined position and orientation at the measurement station during each of the steps.

4. The method as claimed in claim 1, wherein the part axis is defined as being central to the part and parallel to its length.

5. The method as claimed in claim 1, further comprising projecting focused lines of radiation at the top and bottom end surfaces of the held part to obtain reflected radiation and sensing the reflected radiation to obtain electrical signals which represent a depth feature of the part.

6. The method as claimed in claim 1, wherein the beams of radiation at the top and bottom end surfaces are strobed.

7. A system for optically inspecting the ends of a manufactured part at a single inspection station having a measurement axis, the system comprising:
  a fixture assembly including:
    a rotatable first fixturing component, the part having opposite top and bottom ends with top and bottom end surfaces, respectively, a length between the ends, a width and a part axis; and
    a rotatable second fixturing component removably connected to the first fixturing component to transmit torque from the first fixturing component to the second fixturing component, the second fixturing component including a device for holding the part in a generally horizontal orientation and permit rotation of the horizontally held part between first and second angular positions about the measurement axis;
  an actuator assembly to rotatably drive the first fixturing component about the measurement axis and to rotatably drive the second fixturing component about the measurement axis between the first and second angular positions when the second fixturing component is connected to the first fixturing component;
  an illumination device to direct a beam of radiation at the top end surface of the horizontally held part at the first angular position and at the bottom end surface of the horizontally held part at the second angular position to obtain first and second reflected beams, respectively;
  a lens and detector assembly to image and detect the reflected beams to obtain electrical signals; and
  at least one processor to process the electrical signals to determine at least one geometric dimension or any visual defects at the ends of the part.

8. The system as claimed in claim 7, wherein the lens and detector assembly has a predetermined position, orientation and field of view at the inspection station and wherein the second fixturing component holds the part inside the predetermined field of view in the first and second angular positions.

9. The system as claimed in claim 7, wherein the first and second reflected beams are detected at a single image plane of the lens and detector assembly.

10. The system as claimed in claim 7, wherein the part axis is defined as being central to the part and parallel to its length.

11. The system as claimed in claim 7, further comprising an optical depth sensor to sense a depth feature of the part.

12. The system as claimed in claim 11, wherein the depth sensor includes a triangulation-based sensor configured to project focused lines of radiation at the top and bottom end surfaces of the held part and to sense corresponding reflected lines of radiation to obtain electrical signals.

13. The system as claimed in claim 7, wherein the beams of radiation are strobed.

14. The system as claimed in claim 7, wherein the illumination device includes an array of spaced light sources.

15. The system as claimed in claim 14, wherein each of the light sources is a light emitting diode.

16. The system as claimed in claim 14, wherein the light sources are arranged in a generally curved arrangement.

17. The system as claimed in claim 7, wherein the actuator assembly includes an electrically-powered, rotary actuator.

18. The system as claimed in claim 7, wherein the first fixturing component comprises a mating tool.

19. The system as claimed in claim 18, wherein the tool comprises a recess bit.

20. The system as claimed in claim 7, wherein the device comprises a V-block.

* * * * *